(12) United States Patent
Aizawa

(10) Patent No.: US 12,004,873 B2
(45) Date of Patent: Jun. 11, 2024

(54) INFORMATION PROCESSING DEVICE, AND METHOD OF VENTILATING INFORMATION PROCESSING DEVICE

(71) Applicant: SONY CORPORATION, Tokyo (JP)

(72) Inventor: Kota Aizawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 1047 days.

(21) Appl. No.: 16/635,218

(22) PCT Filed: Jul. 26, 2018

(86) PCT No.: PCT/JP2018/028030
§ 371 (c)(1),
(2) Date: Jan. 30, 2020

(87) PCT Pub. No.: WO2019/031256
PCT Pub. Date: Feb. 14, 2019

(65) Prior Publication Data
US 2020/0367819 A1 Nov. 26, 2020

(30) Foreign Application Priority Data

Aug. 8, 2017 (JP) ................................. 2017-153127

(51) Int. Cl.
*A61B 5/00* (2006.01)
*A61B 5/021* (2006.01)
(Continued)

(52) U.S. Cl.
CPC .............. *A61B 5/681* (2013.01); *B01J 20/14* (2013.01); *F26B 5/00* (2013.01); *A61B 5/02108* (2013.01);
(Continued)

(58) Field of Classification Search
CPC . A61B 5/681; A61B 5/02108; A61B 5/02416; A61B 5/165; A61B 5/4266;
(Continued)

(56) References Cited

U.S. PATENT DOCUMENTS

2016/0143584 A1   5/2016  Inagaki
2018/0020966 A1*  1/2018  Begtrup .................. A61B 5/01
                                                  600/301

FOREIGN PATENT DOCUMENTS

CN      102499663 A     6/2012
JP      05-003875 A     1/1993
(Continued)

OTHER PUBLICATIONS

International Search Report and Written Opinion of PCT Application No. PCT/JP2018/028030, dated Aug. 28, 2018, 10 pages of ISRWO.

*Primary Examiner* — Michael C Zarroli
(74) *Attorney, Agent, or Firm* — CHIP LAW GROUP

(57) ABSTRACT

The present technology relates to an information processing device and a method of ventilating an information processing device, which are able to prevent getting sweaty and damp when the information processing device is worn. The information processing device is to be worn by a user and includes a main body portion having a contact surface that is brought into contact with a skin of the user, and a groove that crosses the contact surface. The present technology is able to be applied to a wearable device of a type such as a wrist-band type, an earphone type, a neckband type, an eyeglasses type, a watch type, a bracelet type, a neckless type, a headset type, or a head-mount type.

21 Claims, 39 Drawing Sheets

(51) Int. Cl.
  *A61B 5/024* (2006.01)
  *A61B 5/16* (2006.01)
  *B01J 20/14* (2006.01)
  *F26B 5/00* (2006.01)

(52) U.S. Cl.
  CPC ........... *A61B 5/02416* (2013.01); *A61B 5/165* (2013.01); *A61B 5/4266* (2013.01); *A61B 5/4809* (2013.01); *A61B 2560/0406* (2013.01)

(58) Field of Classification Search
  CPC .......... A61B 5/4809; A61B 2560/0406; A61B 2562/14; A61B 2562/16; A61B 2562/245; A61B 5/14517; B01J 20/14; F26B 5/00
  See application file for complete search history.

(56) References Cited

FOREIGN PATENT DOCUMENTS

| | | |
|---|---|---|
| JP | 2008-086364 A | 4/2008 |
| JP | 2008-168054 A | 7/2008 |
| JP | 2012-176120 A | 9/2012 |
| JP | 2015-093167 A | 5/2015 |
| JP | 2016-096955 A | 5/2016 |

\* cited by examiner

DIRECTION OF GRAVITY

VENTILATION DETERIORATES IF DEVICE IS WORN IN DIFFERENT DIRECTIONS

THIS CONFIGURATION WORKS EVEN IF DEVICE IS WORN IN EITHER DIRECTIONS

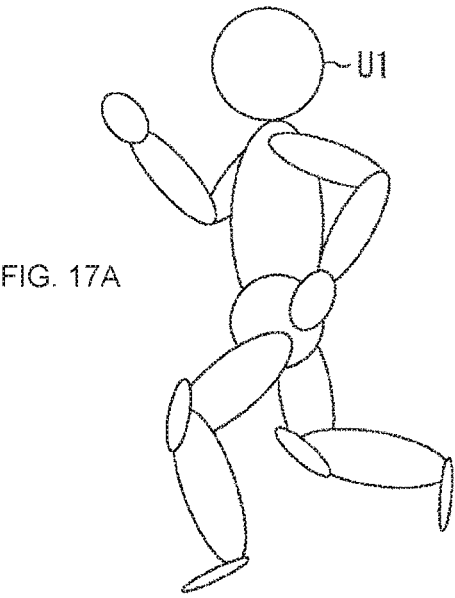
FIG. 17A
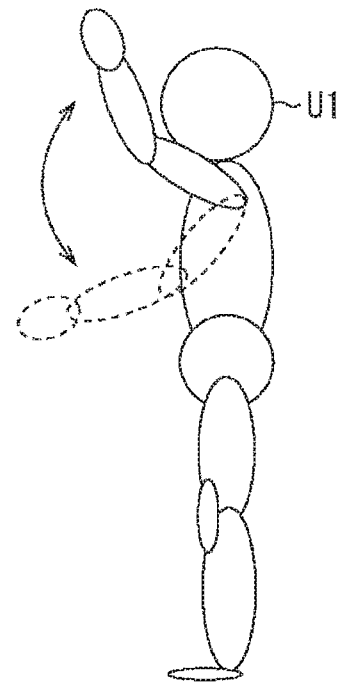
FIG. 17B
DIRECTION OF GRAVITY
FIG. 17C
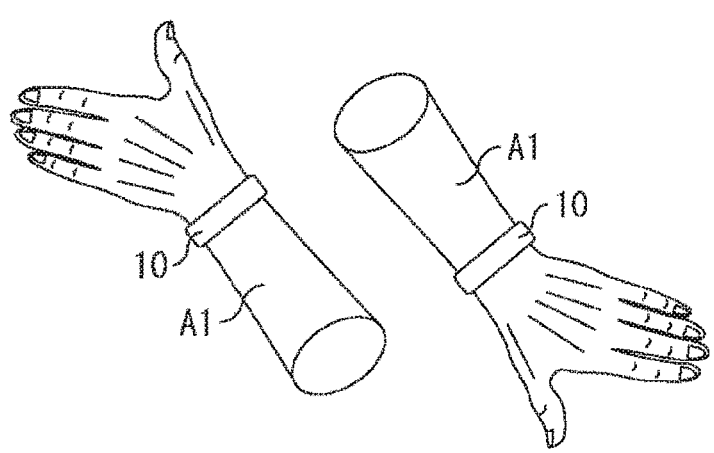

FIG. 28A
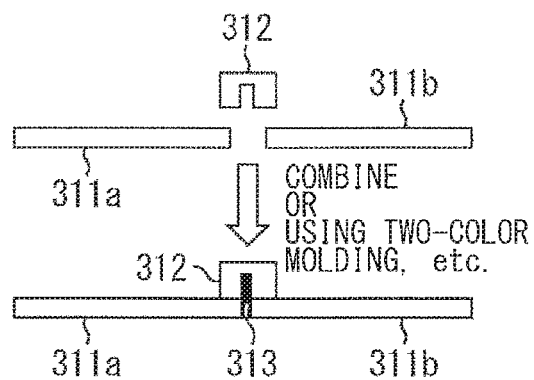
FIG. 28B
FIG. 29
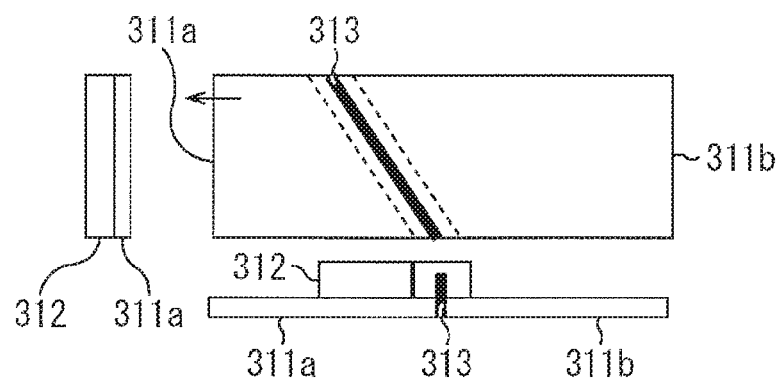

FIG. 34A  BOX IN WHICH ONLY THIS FACE IS OPENED

INFLATES ONLY IN OPENED-FACE SIDE

IT IS POSSIBLE TO CONTROL STATE OF GROOVE BY PROVIDING DOOR

IT IS POSSIBLE TO MAKE GROOVE INTO CURVED SHAPE BY MAKING SHAPE OF DOOR CHANGEABLE

INFORMATION PROCESSING DEVICE, AND METHOD OF VENTILATING INFORMATION PROCESSING DEVICE

CROSS REFERENCE TO RELATED APPLICATIONS

This application is a U.S. National Phase of International Patent Application No. PCT/JP2018/028030 filed on Jul. 26, 2018, which claims priority benefit of Japanese Patent Application No. JP 2017-153127 filed in the Japan Patent Office on Aug. 8, 2017. Each of the above-referenced applications is hereby incorporated herein by reference in its entirety.

TECHNICAL FIELD

The present technology relates to an information processing device, and a method of ventilating an information processing device, and in particular, relates to an information processing device, and a method of ventilating an information processing device, which are configured to prevent getting sweaty and damp when worn.

BACKGROUND ART

Measures have been taken against getting sweaty and damp for a sensor that is brought into contact with a skin of a user to detect biological information.

For example, proposal has been made for a sweat sensor to include two exposed electrodes having a raised shape and brought into contact with a body surface, and also include a ventilating hole between the exposed electrodes (see, for example, PTL 1).

Furthermore, proposal has been made for a biological sensor including a detecting unit that is disposed between a both-sides-adhesive body and a covering body and acquires biological data. The both-sides-adhesive body or covering body has a ventilating hole, thereby enhancing moisture permeability (see, for example, PLT 2).

CITATION LIST

Patent Literature

PTL 1: Japanese Unexamined Patent Application Publication No. H05-3875 PTL 2: Japanese Unexamined Patent Application Publication No. 2015-93167

SUMMARY OF THE INVENTION

Problem to be Solved by the Invention

Meanwhile, wearable devices have received attention in recent year, and are worn by users all the time to detect and record a lifelog such as biological information. Such a wearable device is worn for a long period of time. Thus, there is an increasing demand for a wearable device having a measure against getting sweaty and damp.

The present technology has been made in view of the circumstances described above, and aims to prevent getting sweaty and damp at the time of wearing an information processing device.

Means for Solving the Problem

An information processing device according to a first embodiment of the present technology is to be worn by a user, and includes: a main body portion having a first contact surface that is brought into contact with a skin of the user; and a groove that crosses the first contact surface.

A method of ventilating an information processing device according to a second embodiment of the present technology includes providing, on a contact surface of the information processing device to be worn by a user, a groove that crosses the contact surface, in which the contact surface is brought into contact with a skin of the user.

According to the first and the second embodiments of the present technology, sweat and moisture on and around the contact surface that is to be brought into contact with the skin of a user are caused to run away.

Effects of the Invention

According to the first and second embodiments of the present technology, it is possible to prevent getting sweaty and damp at the time of wearing the information processing device.

It should be noted that the effect described here is not given for the purpose of limitation. Any effects described in the present disclosure may be taken.

BRIEF DESCRIPTION OF THE DRAWINGS

FIGS. 17A, 17B, and 17C are diagrams illustrating an example in which the wearable device is used.

FIGS. 28A and 28B are diagrams used to describe a method of coupling sheets and a coupling member.

FIG. 29 is a diagram used to describe a method of changing a state of the groove.

FIGS. 34A, 34B, and 34C are diagrams used to describe a method of changing a shape of a balloon.

MODES FOR CARRYING OUT THE INVENTION

Below, embodiments of the present technology will be described. Description will be given in the following order.
1. First Embodiment (Example in which a state of a groove is fixed)
2. Second Embodiment (Example in which a state of a groove is variable)
3. Modification examples
4. Others 1. First Embodiment First, a first embodiment according to the present technology will be described with reference to FIGS. 1A, 1B, 2, 3, 4, 5, 6, 7A, 7B, 8A 8B, 8C, 9, 10, 11A, 11B, 12A, 12B, 13A, 13B, 14, 15, 16A, 16B, 17A, 17B, 17C, 18, 19A, 19B, 20A, 20B, 21A, 21B, 21C, 22, 23, 24, 25, and 26.

Example of Configuration of Wearable Device

Figure 1B:
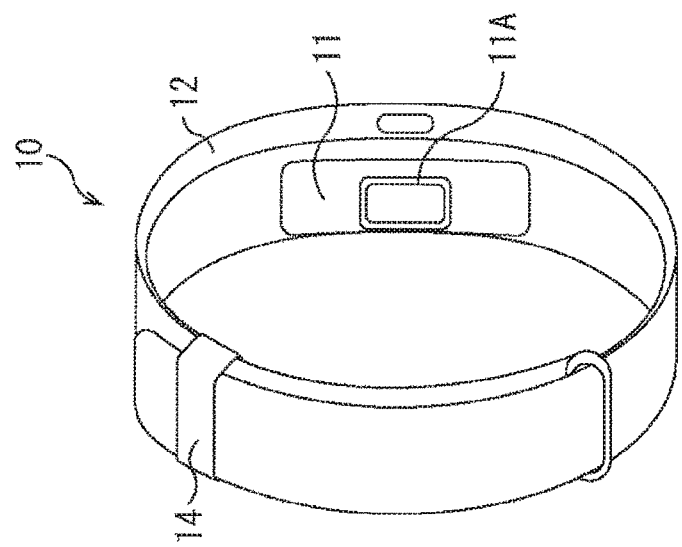
FIGS. 1A and 1B are schematic views of an example of a configuration of external appearance concerning a first embodiment of a wearable device to which the present technology is applied.
Figure 1A:
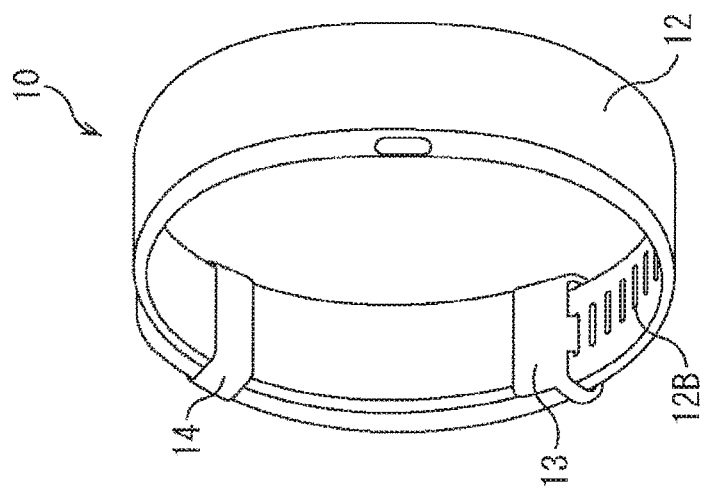

FIGS. 1A and 1B are diagrams illustrating an example of a configuration of external appearance concerning a wearable device 10 to which the present technology is applied.

The wearable device 10 includes a wrist-band type wearable device. The wearable device 10 includes a device section 11, a band 12, a buckle 13, and a band loop 14. The wearable device 10 is worn on the wrist of a user using the band 12 serving as a wearing unit. The wearable device 10 is fixed on the wrist using an attachment hole 12A of the band 12, the buckle 13, and the band loop 14.

The device section 11 serves as a main body portion of the wearable device 10. For example, the device section 11 includes, within a housing thereof, various electronic parts used to achieve functions of the wearable device 10, the electronic parts including, for example, a processor that performs various types of processes, various types of sensors, a communicating part that performs communication with the outside, and a storage medium. The device section 11 includes a body including, for example, resin such as plastic.

For example, the device section 11 includes, therein, an acceleration sensor, a pulse wave sensor (for example, photoplethysmography), a sweat sensor, an optical sensor, and the like to detect, for example, acceleration, pulse waves, and the amount of sweat of the user. In addition, the device section 11 detects various types of biological information such as steps the user takes, energy consumption, sleeping hours, sleeping states, and emotions (for example, stress levels or the like), on the basis of detection results. The device section 11 records the detected biological information or sends it to the outside as necessary.

Furthermore, for example, the device section 11 includes a vibrator or the like therein to notify various types of information. For example, in liaison with a mobile information terminal such as a smartphone or a mobile phone apparatus, the device section 11 notifies the user of reception of an email, news, or the like to the mobile information terminal, and a schedule registered in the mobile information terminal, by vibration or the like.

In addition, the device section 11 is disposed at a contact surface that is disposed on the inner side of the band 12 and is brought into contact with a skin of the user. The contact surface is exposed toward the inner side, and is brought into contact with the skin of the user. The device section 11 includes a contact surface including a raised portion 11A as necessary.

It should be noted that the device section 11 may be fixed to the band 12 or may be provided detachably from the band 12.

Furthermore, hereinafter, the contact surface of the device section 11 and the contact surface of the band 12 are collectively referred to as a contact surface of the wearable device 10.

The band 12 includes, for example, silicon. Note that the band 12 may have a front surface including a display used to display various types of information.

It should be noted that a direction in which the band 12 of the wearable device 10 extends (a direction in which it is wound around the wrist of a user) is hereinafter referred to as a circumferential direction. In addition, a direction perpendicular to the circumferential direction (a direction in which the arm of the user wearing the wearable device 10 extends) is referred to as a width direction. Furthermore, a position where a straight line extending in the width direction and passing through the middle of the contact surface of the device section 11 intersects a side of the contact surface of the band 12 in the circumference direction is set as a middle.

<Method of Preventing Sweat and Steam>

Next, a method of preventing the wearable device 10 from getting sweaty and damp will be described with reference to FIGS. 2 to 5.

Figure 2:
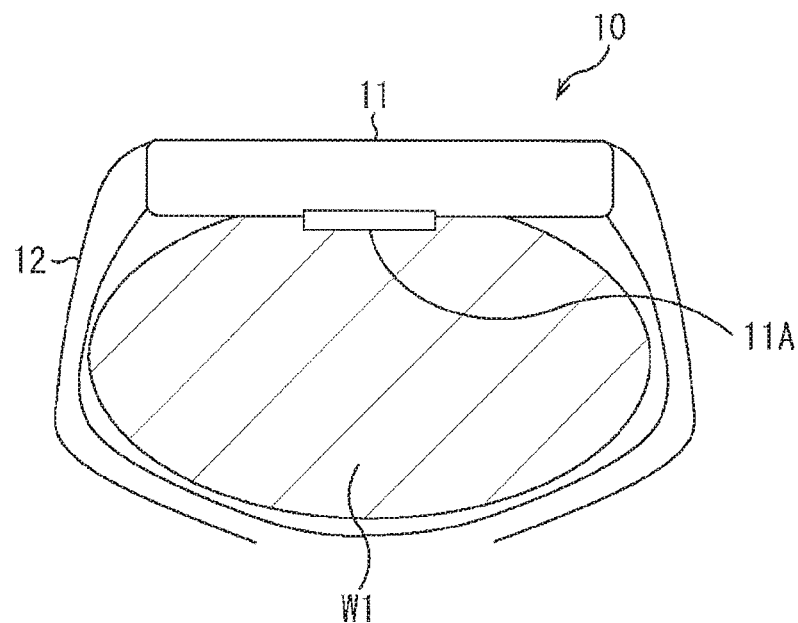
FIG. 2 is a schematic view of an example in which the wearable device is worn.
Figure 3:
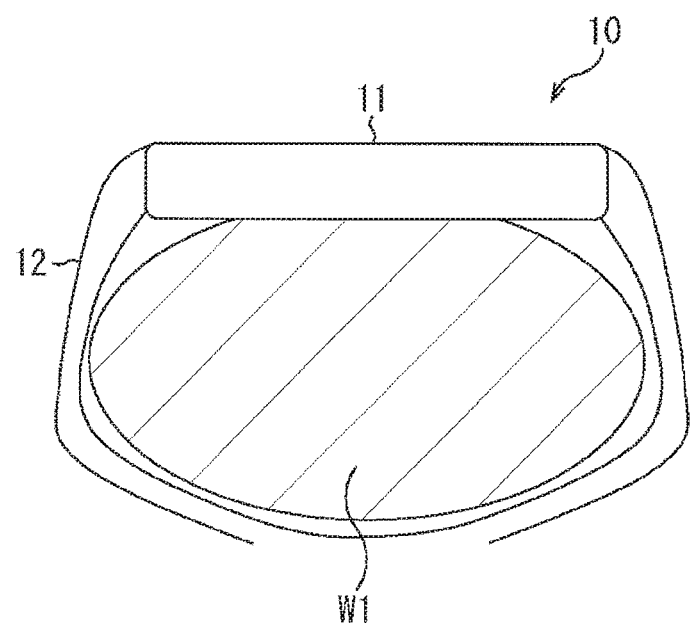
FIG. 3 is a schematic view of an example in which the wearable device is worn.
Figure 4:
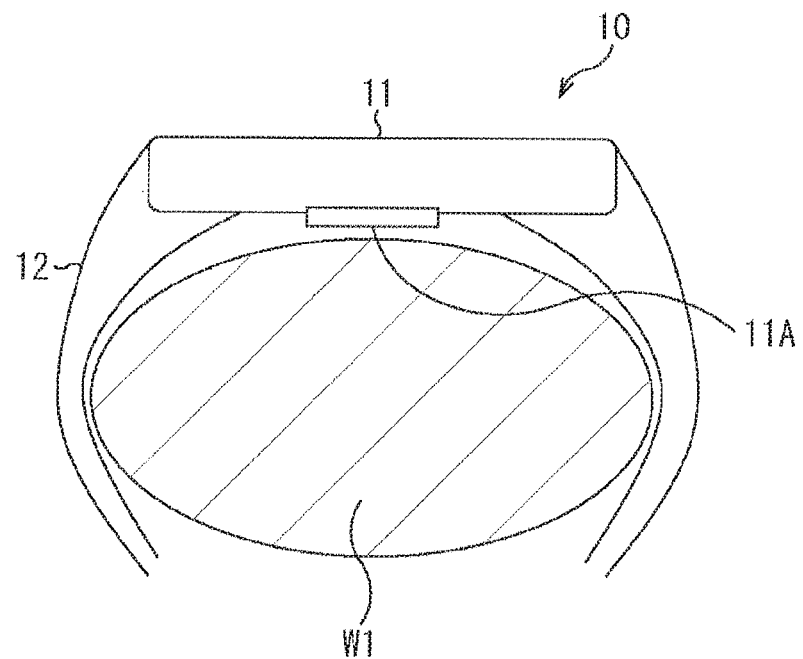
FIG. 4 is a schematic view of an example in which the wearable device is worn.

FIGS. 2 to 4 are schematic views of a manner in which the wearable device 10 is worn on a wrist W1 of a user. Note that FIGS. 2 and 4 illustrate a case where the raised portion 11A is provided on the contact surface of the device section 11. FIG. 3 illustrates a case where no raised portion 11A is provided on the contact surface of the device section 11.

For example, as illustrated in FIGS. 2 and 3, in a case where the wearable device 10 is tightly worn on the wrist W1 of a user, the contact surface of the device section 11 and the contact surface of the band 12 are in close contact with the skin of the user. Depending on the degree of tightness of the band 12, the contact surface of the device section 11 may possibly bite into the skin. In addition, with increase in a period of time when the wearable device 10 is worn, sweat or moisture may possibly accumulate on a portion (hereinafter, referred to as a "contact portion") where the contact surface of the wearable device 10 and the skin are in contact with each other, which leads to discomfort for the user due to being steamy or sticky.

In this case, for example, it is possible to consider that the band 12 is loosely worn as illustrated in FIG. 4. This decreases the degree of contact of the wearable device 10 with the skin, which reduces occurrence of getting sweaty and damp.

However, in a case where the device section 11 includes, for example, a pulse wave sensor, a sweat sensor, or other sensors that detect biological information concerning the surface of or the inside of the skin of the user, it is desirable for the contact surface of the device section 11 to be brought into close contact with the wrist W1 as much as possible in order to enhance the accuracy or sensitivity of detection. In particular, in a case where the arm of the user frequently moves or largely moves such as during physical activities or the like, it is desirable for the wearable device 10 to be tightly worn on the wrist W1 of the user so that the position of the device section 11 does not misaligned.

Thus, a measure is taken for the wearable device 10, the measure being to prevent the contact portion from getting sweaty and damp due to sweat or moisture staying on the contact portion.

For example, a material having an excellent water repellency, ventilation, rapid drying property, moisture-absorbing property, or the like, or processing that provides these properties is used for the contact surface of the device section 11 or the contact surface of the band 12.

For example, a diatomaceous earth having an increased rapid drying property is used for the contact surface of the device section 11.

For example, processing that provides a lotus effect with excellent water repellency is applied to the contact surface of the device section 11 or the contact surface of the band 12.

For example, the band 12 has a multiple layer structure. Meshing processing is applied to the contact surface thereof. A water absorbing layer is provided as a layer on or above the meshing to make sweat absorbed therewith.

In addition, in the wearable device 10, the contact surface of the device section 11 and the contact surface of the band 12 have a mechanism that allows sweat to run away. Specifically, the contact surface of the device section 11 and the contact surface of the band 12 include a ventilating groove that allows sweat to run away.

Figure 5:
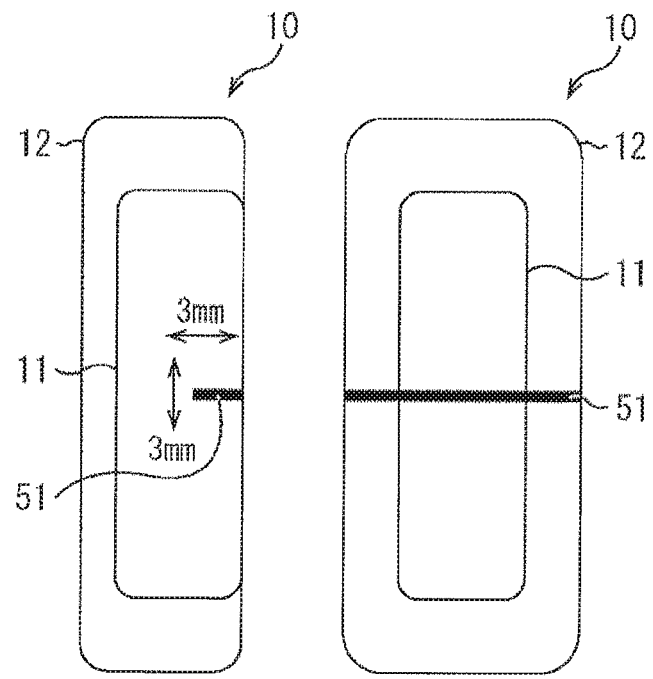
FIG. 5 is a diagram illustrating a first embodiment of a groove of the wearable device.

FIG. 5 is a diagram schematically illustrating the contact surface of the device section 11 of the wearable device 10 and the vicinity of the contact surface. A diagram on the left side in FIG. 5 is a schematic view of cross section of the device section 11 and the band 12. A diagram on the right side in FIG. 5 is a schematic view on and around the contact surface of the device section 11 when viewed from above.

In this example, the contact surface of the device section 11 and the contact surface of the band 12 have a ventilating groove 51 formed to prevent getting sweaty and damp.

The groove 51 has a width of, for example, about 3 mm and a depth of, for example, about 3 mm. Note that, in this drawing, for the purpose of facilitating understanding of the position of the groove 51, the groove 51 is illustrated to be larger than the actual size. In particular, the depth thereof is illustrated to be longer than the width. This similarly applies to the following drawings. In addition, in the following drawings, the width of and the depth of a groove or each groove are each set to be about 3 mm unless otherwise specified.

The groove 51 passes through the middle of the contact surface of the device section 11. The groove 51 has a straight-line shape perpendicular to the circumferential direction. The groove 51 crosses the contact surface of the device section 11 and the contact surface of the band 12 in the width direction. Furthermore, the sweat and moisture staying on and around the contact portion between the device section 11 and the skin of the user are caused to run away through the groove 51. This makes it possible to prevent getting sweaty and damp.

It should be noted that a rate of close contact with the skin of a user increases toward the middle of the contact surface of the device section 11 in the circumferential direction. Thus, providing the groove 51 at the middle of the contact surface of the device section 11 in the circumferential direction enhances the effect of causing sweat or moisture to run away. In addition, the groove 51 crosses the contact surface of the device section 11 and the contact surface of the band 12 in the shortest way between sides of the contact surfaces in the longitudinal direction (in the circumferential direction). This makes sweat or moisture less likely to stay in the groove 51. In addition, the groove 51 has a narrow width, and area of the contact surface of the device section 11 is substantially unchanged. Thus, for example, it is possible to keep favorable detection accuracy of sensors built in the device section 11.

Modification Example of Ventilating Groove

It should be noted that the number, the position, the direction, the shape, and the like of ventilating grooves of the wearable device 10 may be changed as appropriate on the basis of the shape of the contact surface of the device section 11 and the contact surface of the band 12, a portion of a user to be brought into contact with the contact surface, the position and the direction of the contact surface with respect to the portion, movement of the portion, a direction of force at the portion, and the like.

Below, a modification example of the ventilating groove of the wearable device 10 will be described.

Figure 6:
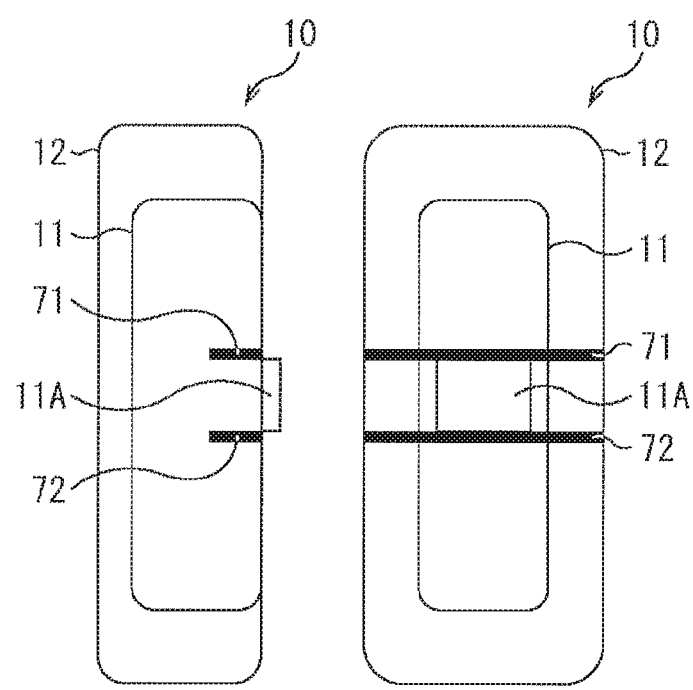
FIG. 6 is a diagram illustrating a second embodiment of a groove of the wearable device.

FIG. 6 illustrates an example of a case in which the raised portion 11A is provided on the contact surface of the device section 11. A diagram on the left side in FIG. 6 is a schematic view of cross section of the device section 11 and the band 12, as with the diagram on the left side in FIG. 5. A diagram on the right side in FIG. 6 is a schematic view on and around the contact surface of the device section 11 when viewed from above, as with the diagram on the right side in FIG. 5.

In this example, two lines of a groove 71 and a groove 72 that are in parallel are provided on the contact surface of the wearable device 10.

Specifically, the groove 71 is provided along a side of the raised portion 11A on one side (upper side in the drawing) in the width direction so as to cross the contact surface of the device section 11 and the contact surface of the band 12 in the width direction. The groove 72 is provided along a side of the raised portion 11A on the other side (lower side in the drawing) in the width direction so as to cross the contact surface of the device section 11 and the contact surface of the band 12 in the width direction.

Furthermore, the sweat and moisture staying on and around the contact portion between the device section 11 and the skin of the user are caused to run away through the groove 71 and the groove 72 to the outside to prevent getting sweaty and damp. In particular, sweat and moisture tend to stay on and around the raised portion 11A of the device section 11. Thus, by providing the groove 71 and the groove 72 along the periphery of the raised portion 11A, it is possible to more effectively cause the sweat and moisture staying on and around the raised portion 11A to run away.

Figure 7A:
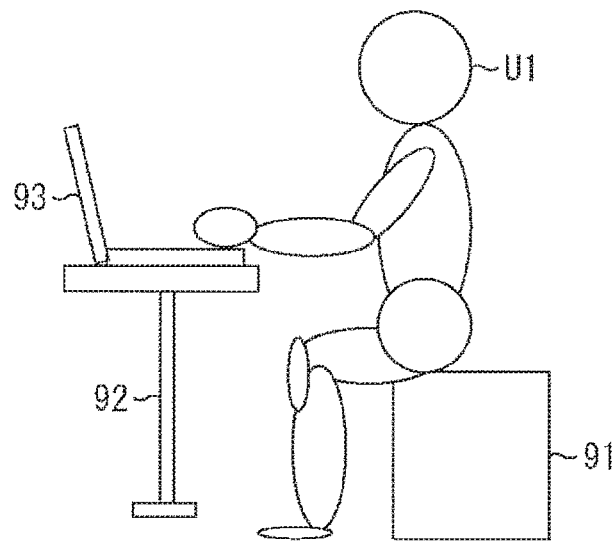
FIGS. 7A and 7B are diagrams illustrating an example in which the wearable device is used.
Figure 7B:
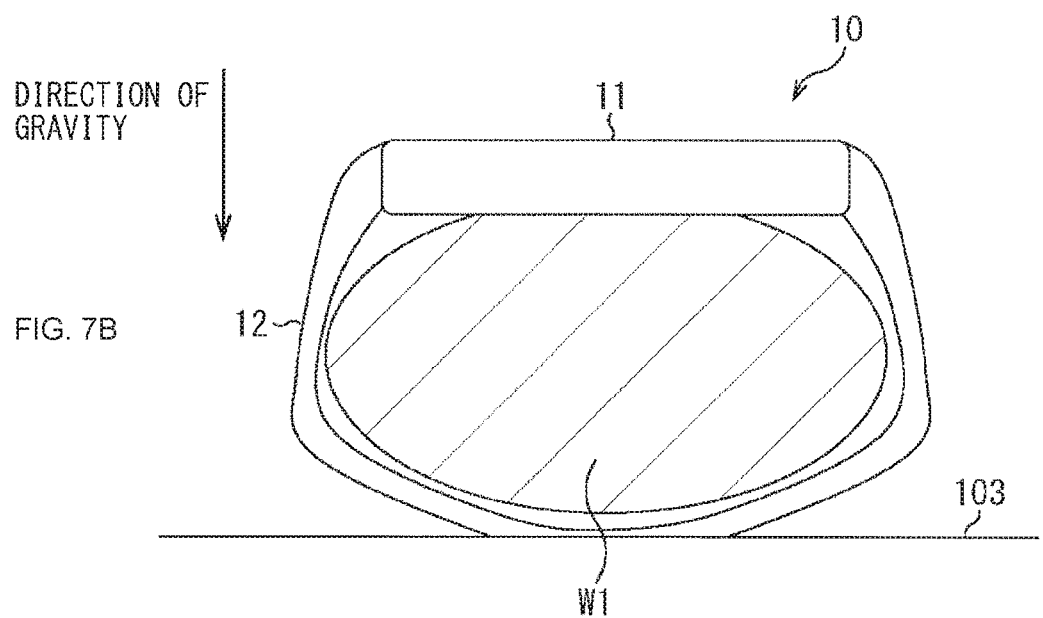

Here, for example, in a case where a user U1 is sitting on a chair 91 to manipulate a personal computer (PC) 93 on a desk 92 as illustrated in FIG. 7A, the wearable device 10 is in a state as illustrated in FIG. 7B. That is, the device section 11 is disposed above the wrist W1 of the user U1. The contact surface of the device section 11 faces a direction substantially equal to the gravity.

In this case, by providing a groove or grooves as illustrated, for example, in FIGS. 5 and 6, it is possible to cause the sweat and moisture to effectively run away from the contact portion between the device section 11 and the skin of the user.

Figure 8A:
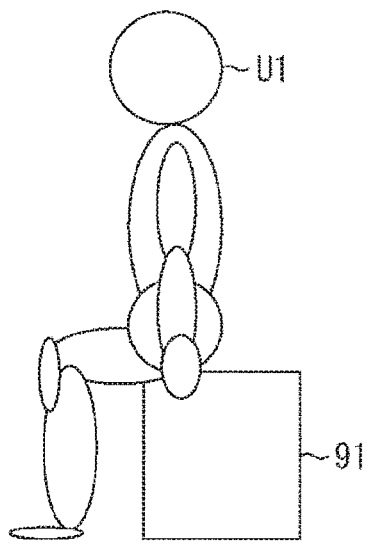
FIGS. 8A, 8B, and 8C are diagrams illustrating an example in which the wearable device is used.
Figure 8B:
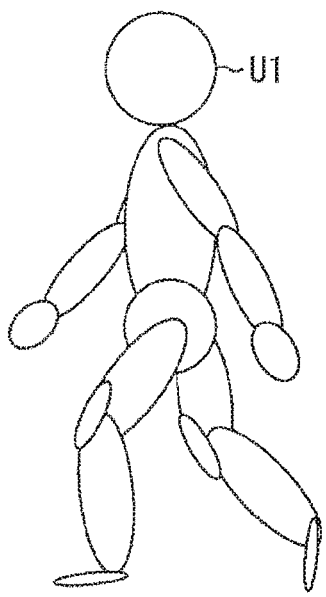
Figure 8C:
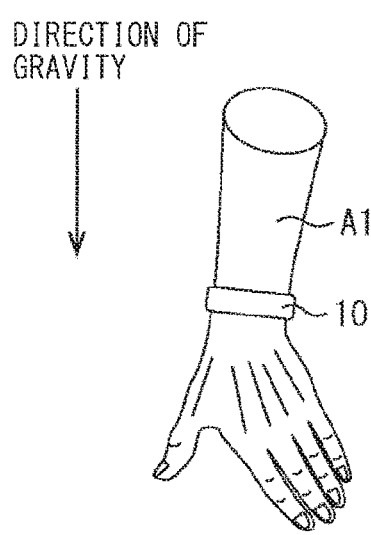

Furthermore, in a case where the user U1 is sitting on the chair 91 as illustrated in FIG. 8A, or in a case where the user U1 is walking as illustrated in FIG. 8B, the arm A1 of the user U1 is generally in a state of extending downward as illustrated in FIG. 8C.

Figure 9:
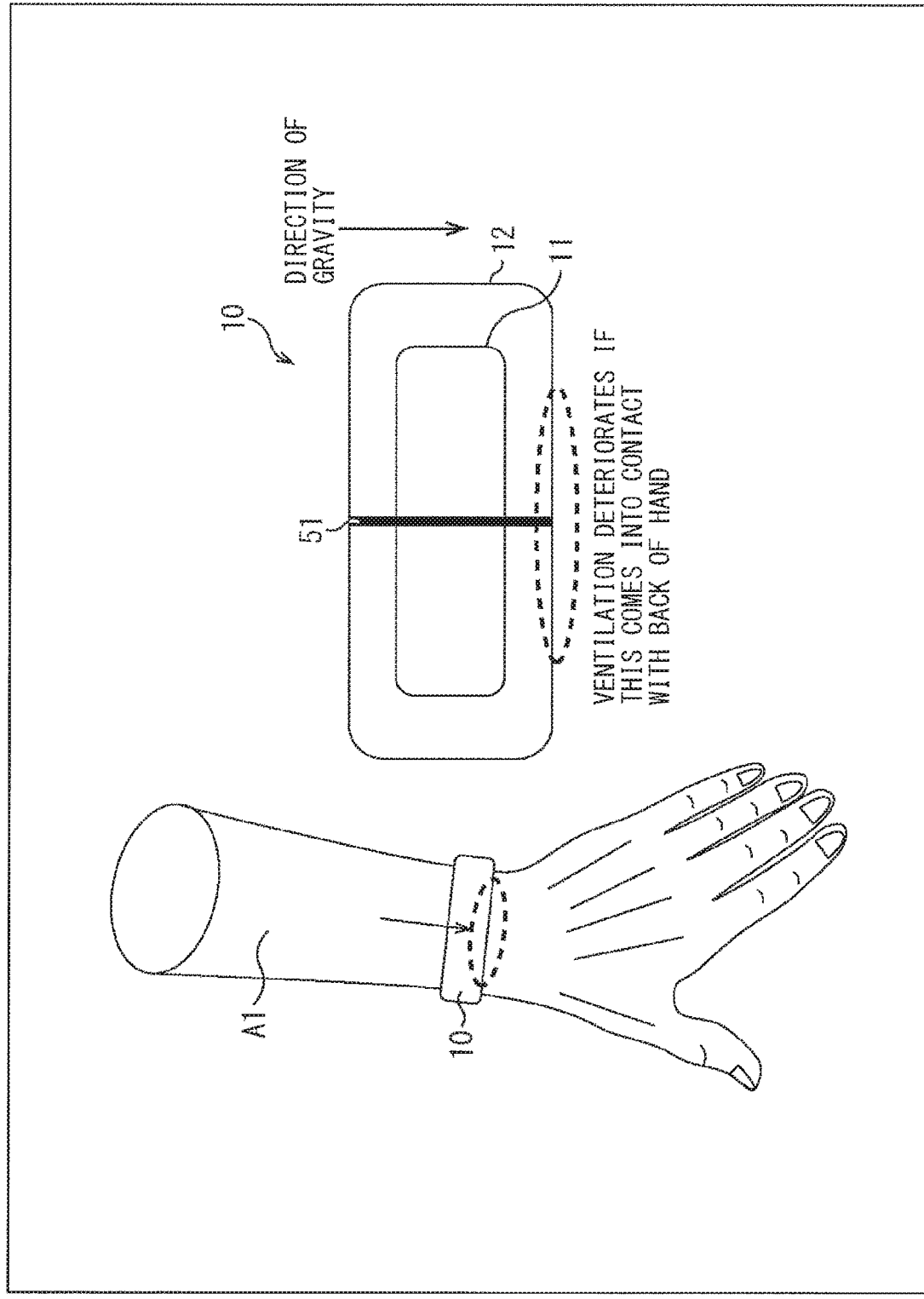
FIG. 9 is a diagram illustrating an example in which ventilation of a groove of the wearable device gets deteriorated.

In this case, there is a possibility that the side surface of the band 12 of the wearable device 10 on the lower side in the circumferential direction is brought into contact with the back of user's hand, as illustrated in the left side of FIG. 9. Upon being into contact with the back of user's hand, the back of user's hand blocks the end portion of the groove 51, which possibly leads to a deterioration of ventilation.

Figure 10:
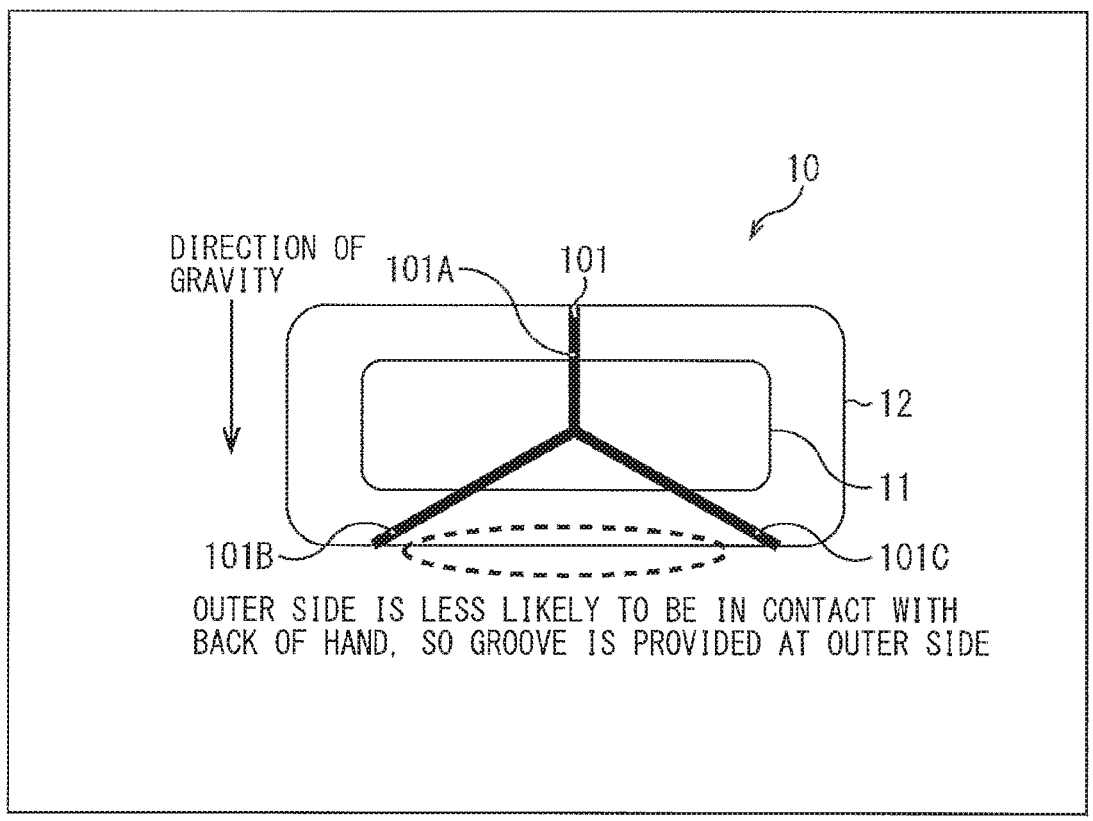
FIG. 10 is a diagram illustrating a third embodiment of a groove of the wearable device.

It is possible to consider that the groove is shaped as illustrated in FIG. 10 in order to prevent the deterioration of ventilation.

Specifically, a groove 101 branches at the middle of the contact surface of the device section 11 into three directions: a groove 101A to a groove 101C.

The groove 101A extends from the middle of the contact surface of the device section 11 to the middle of a side of the contact surface of the band 12, the side being on one side (upper side in the drawing) in the circumferential direction. The groove 101B extends toward a diagonal direction from the middle of the contact surface of the device section 11 to a side of the contact surface of the band 12, the side being on the other side (lower side in the drawing) in the circumferential direction. The groove 101C extends diagonally in a direction opposite to the direction of the groove 101B from the middle of the contact surface of the device section 11 to a side of the contact surface of the band 12, the side being on the other side (lower side in the drawing) in the circumferential direction. Thus, the space between the groove 101B and the groove 101C widens toward the side of the device section 11 and the side of the band 12 on the back side of user's hand.

This makes the end portions of the groove 101B and the groove 101C disposed at positions spaced apart from the middle of the side of the contact surface of the band 12 in the circumferential direction, the positions being spaced apart in directions differing from each other. Meanwhile, the possibility of the side surface of the band 12 in the circumferential direction being brought into contact with the back of user's hand increases toward the middle of this side surface, whereas this possibility decreases away from this middle. Thus, as compared with the end portion of the groove 51 in FIG. 9, the end portions of the groove 101B and the groove 101C are less likely to be blocked by the back of user's hand, which results in favorable ventilation being kept.

Figure 11A:
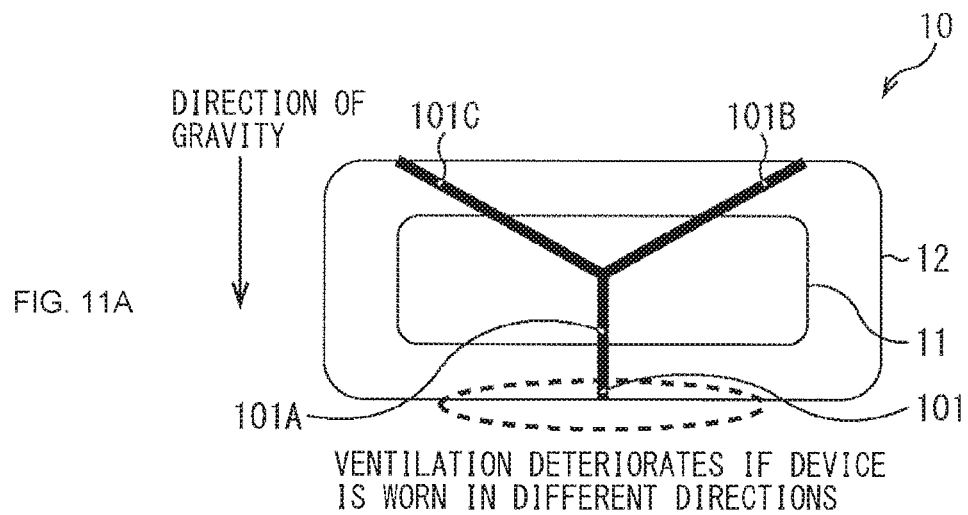
FIGS. 11A and 11B are diagrams illustrating a fourth embodiment of a groove of the wearable device.

However, for example, in a case where, as illustrated in FIG. 11A, the wearable device 10 is worn in a direction inverted to that in FIG. 10, the position of the end portion of the groove 101A relative to the back of user's hand is similar to the position of the end portion of the groove 51 relative to the back of user's hand illustrated in FIG. 9. This may lead to the end portion of the groove 101A being blocked by the back of user's hand, which results in a deterioration of ventilation.

Figure 11B:
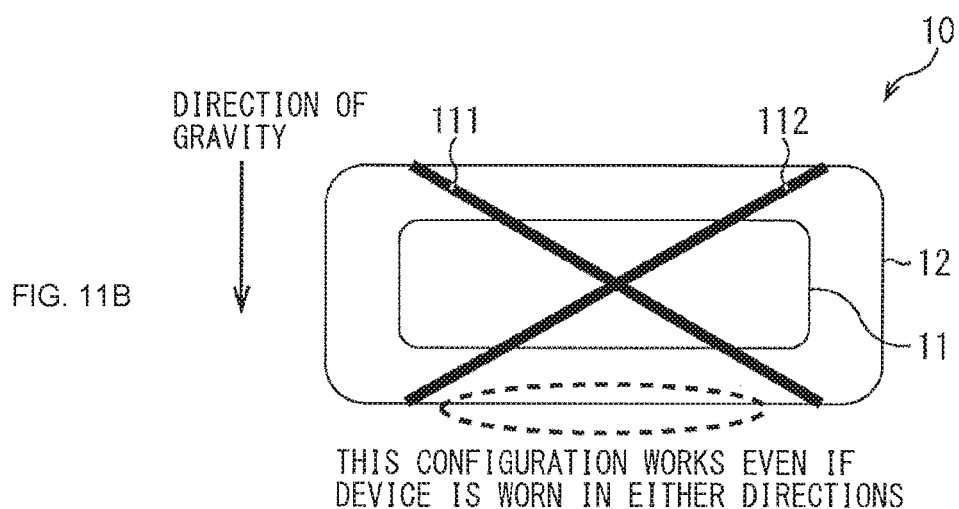

For this case, for example, it is possible to consider that the groove is shaped as illustrated in FIG. 11B.

Specifically, a groove 111 diagonally crosses between two sides of the contact surface of the band 12 in the circumferential direction. A groove 112 diagonally crosses between two sides of the contact surface of the band 12 in the circumferential direction, the crossing being in a direction symmetrical to the groove 111. In addition, the groove 111 and the groove 112 intersect with each other at the middle of the contact surface of the device section 11.

This makes the end portions of the groove 111 and the groove 112 disposed at positions spaced apart from the middle of the side of the contact surface of the band 12 in the circumferential direction, the positions being spaced apart in directions differing from each other, regardless of a direction in which the wearable device 10 is worn. Thus, the end portions of the groove 111 and the groove 112 are less likely to be blocked by the back of user's hand, which results in favorable ventilation being kept.

Figure 12A:
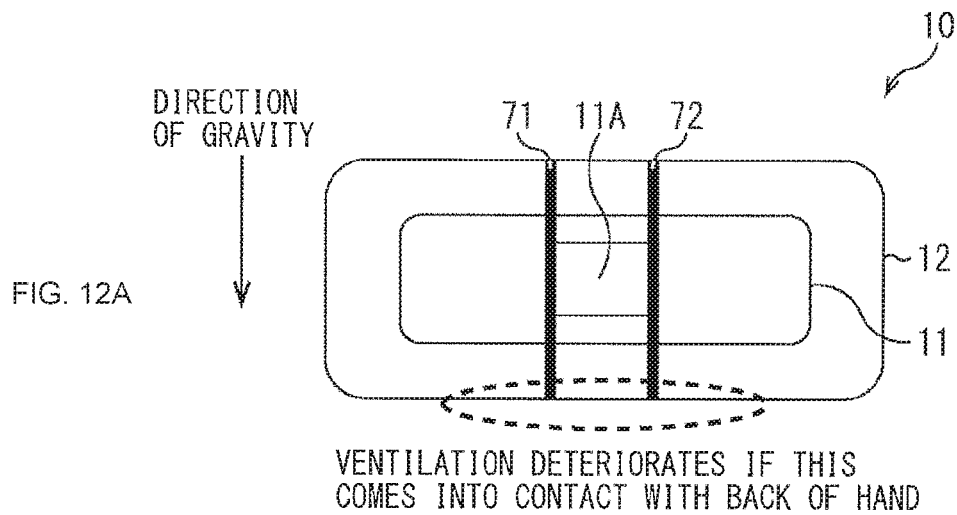
FIGS. 12A and 12B are diagrams illustrating a fifth embodiment of a groove of the wearable device.

Furthermore, in a case of the wearable device 10 described above and illustrated in FIG. 6, there is a possibility that the end portions, on the lower side, of the groove 71 and the groove 72 are blocked by the back of user's hand as illustrated in FIG. 12A, which results in a deterioration of ventilation.

Figure 12B:
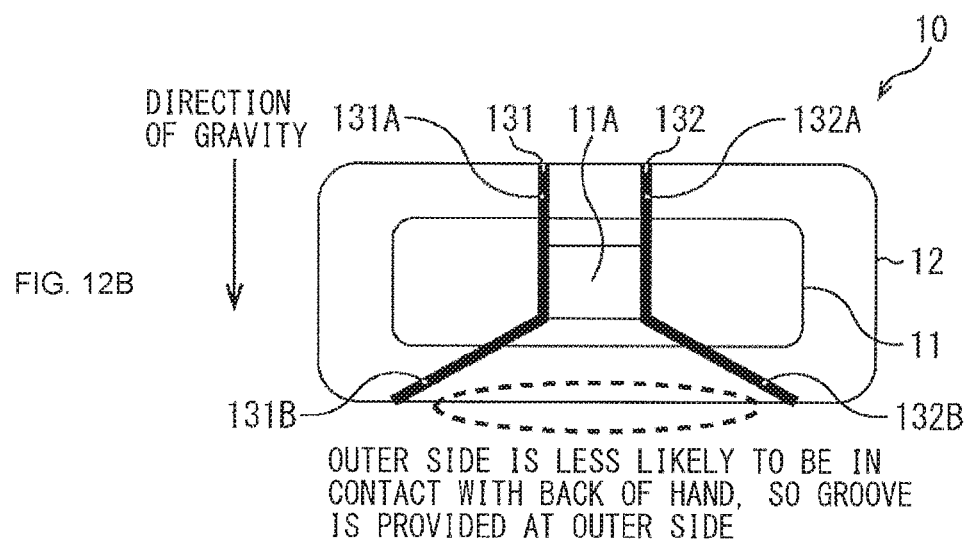

For this case, for example, it is possible to consider that the groove is shaped as illustrated in FIG. 12B.

Specifically, a groove 131 includes a groove 131A and a groove 131B. The groove 131A extends in the width direction from a side of the contact surface of the band 12 on one side (upper side in the drawing) in the circumferential direction, and also extends along a side of the raised portion 11A on one side (left side in the drawing) in the width direction up to the end portion of this side of the raised portion 11A. The groove 131B diagonally extends in a direction away from the raised portion 11A (toward the left side in the drawing), from the end portion of the groove 131A on the raised portion 11A side, and reaches a side of the contact surface of the band 12 on the other side (lower side in the drawing) in the circumferential direction.

The groove 132 includes a groove 132A and a groove 132B. The groove 132A extends in the width direction from a side of the contact surface of the band 12 in the circumferential direction on one side (upper side in the drawing), and extends along a side of the raised portion 11A on the other side (right side in the drawing) in the width direction up to the end portion of this side of the raised portion 11A. The groove 132B diagonally extends in a direction away from the raised portion 11A (toward the right side in the drawing and in a direction symmetrical to the groove 131B), from the end portion of the groove 132A on the raised portion 11A side, and reaches a side of the contact surface of the band 12 on the other side (lower side in the drawing) in the circumferential direction.

This makes the end portions of the groove 131B and the groove 131C disposed at positions spaced apart from the middle of the side of the contact surface of the band 12 in the circumferential direction, the positions being spaced apart in directions differing from each other. Thus, the end portions of the groove 131B and the groove 132B are less likely to be blocked by the back of user's hand as compared with the end portions of the groove 71 and the groove 72 in FIG. 12A, which results in favorable ventilation being kept.

Figure 13A:
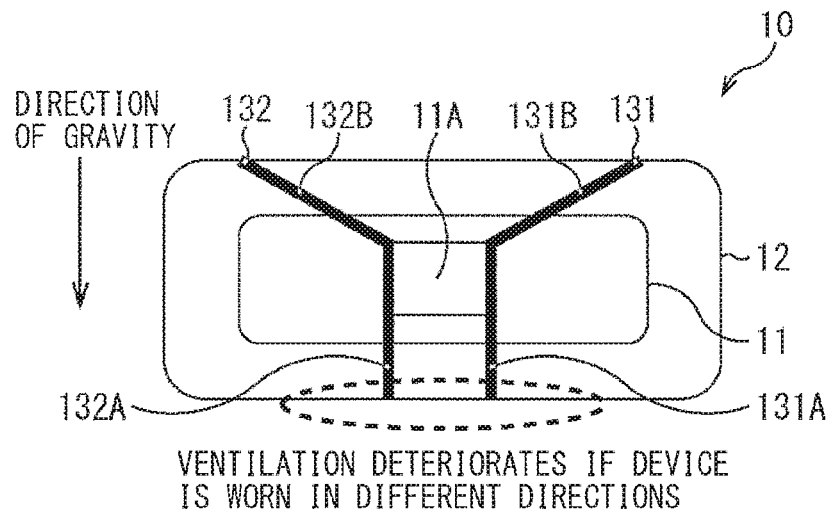
FIG. 13 is a diagram illustrating a sixth embodiment of a groove of the wearable device.

However, for example, in a case where, as illustrated in FIG. 13A, the wearable device 10 is worn in a direction inverted to that in FIGS. 12A and 12B, the positions of the end portions of the groove 131A and the groove 132A are similar to the positions of the end portions of the groove 71 and the groove 72 relative to the back of user's hand in FIG. 12A. This may lead to the end portions of the groove 131A and the groove 132A being blocked by the back of user's hand, which results in a deterioration of ventilation.

Figure 13B:
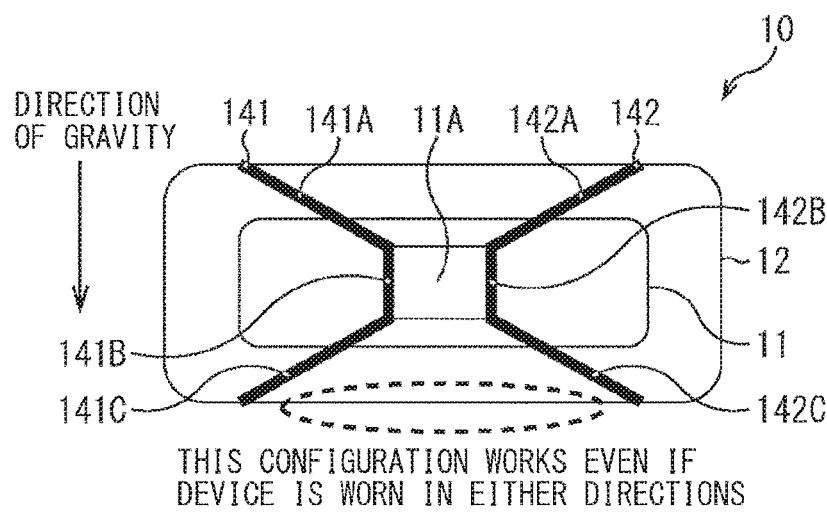

For this case, for example, it is possible to consider that the groove is shaped as illustrated in FIG. 13B.

Specifically, a groove 141 includes grooves 141A to 141C. The groove 141B is formed along a side of the raised portion 11A on one side (left side in the drawing) in the width direction. The groove 141A diagonally extends in a direction away from the raised portion 11A (toward the left side in the drawing), from the end portion of the groove 141B on one side (upper side in the drawing), and reaches a side of the contact surface of the band 12 on one side (upper side in the drawing) in the circumferential direction. The groove 141C diagonally extends in a direction away from the raised portion 11A, from the end portion of the groove 141B on the other side (lower side in the drawing), and reaches a side of the contact surface of the band 12 on the other side (lower side in the drawing) in the circumferential direction.

A groove 142 includes grooves 142A to 142C. The groove 142B is formed along a side of the raised portion 11A on the other side (right side in the drawing) in the width direction. The groove 142A diagonally extends in a direction away from the raised portion 11A (toward the right side in the drawing and in a direction symmetrical to the groove 141A), from the end portion of the groove 142B on one side (upper side in the drawing), and reaches a side of the contact surface of the band 12 on one side (upper side in the drawing) in the circumferential direction. The groove 142C diagonally extends in a direction away from the raised portion 11A (toward the right side in the drawing and in a direction symmetrical to the groove 141C), from the end portion of the groove 142B on the other side (lower side in the drawing), and reaches a side of the constant surface of the band 12 on the other side (lower side in the drawing) in the circumferential direction.

This makes the end portions of the groove 141 and the groove 142 disposed at positions spaced apart from the middle of the side of the contact surface of the band 12 in the circumferential direction, the positions being spaced apart in directions differing from each other, regardless of a direction in which the wearable device 10 is worn. Thus, the end portions of the groove 141 and the groove 142 are less likely to be blocked by the back of user's hand, which results in favorable ventilation being kept.

Figure 14:
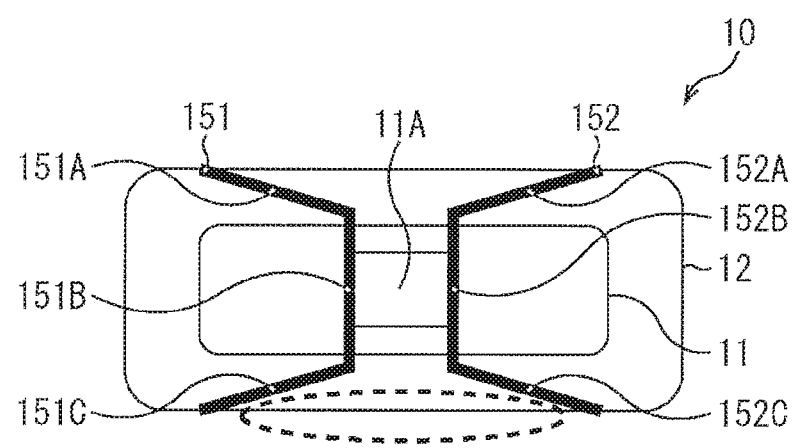
FIG. 14 is a diagram illustrating a seventh embodiment of a groove of the wearable device.

It should be noted that, in the example illustrated in FIG. 13B, illustration is given as an example in which the directions of the groove 141 and the groove 142 are changed at a halfway point in the contact surface of the device section 11. However, the directions may not be changed at a halfway point in the contact surface of the device section 11 as illustrated in FIG. 14

Specifically, a groove 151 includes grooves 151A to 151C. The groove 151B is formed along a side of the raised portion 11A on one side (left side in the drawing) in the width direction, and extends beyond both sides of the contact surface of the device section 11 in the circumferential direction up to a halfway point in the contact surface of the band 12. The groove 151A diagonally extends in a direction away from the raised portion 11A (left side in the drawing), from the end portion of the groove 151B on one side (upper side in the drawing), and reaches a side of the contact surface of the band 12 on one side (upper side in the drawing) in the circumferential direction. The groove 151C diagonally extends in a direction away from the raised portion 11A (left side in the drawing), from the end portion of the groove 151B on the other side (lower side in the drawing), and reaches a side of the contact surface of the band 12 on the other side (lower side in the drawing) in the circumferential direction.

A groove 152 includes grooves 152A to 152C. The groove 152B is formed along a side of the raised portion 11A on one side (right side in the drawing) in the width direction, and extends beyond both sides of the contact surface of the device section 11 in the circumferential direction up to a halfway point in the contact surface of the band 12. The groove 152A diagonally extends in a direction away from the raised portion 11A (toward the right side in the drawing and in a direction symmetrical to the groove 151A), from the end portion of the groove 152B on one side (upper side in the drawing), and reaches a side of the contact surface of the band 12 on one side (upper side in the drawing) in the circumferential direction. The groove 152C diagonally extends in a direction away from the raised portion 11A (toward the right side in the drawing and in a direction symmetrical to the groove 152A), from the end portion of the groove 152B on the other side, and reaches a side of the contact surface of the band 12 on the other side (lower side in the drawing) in the circumferential direction.

In the description above, description has been made by giving an example in which the shape and the like of a groove or grooves are set on the basis of a relationship with the back of user's hand. However, the shape and the like of a groove or grooves may be set on the basis of a direction into which sweat flows.

Figure 15:
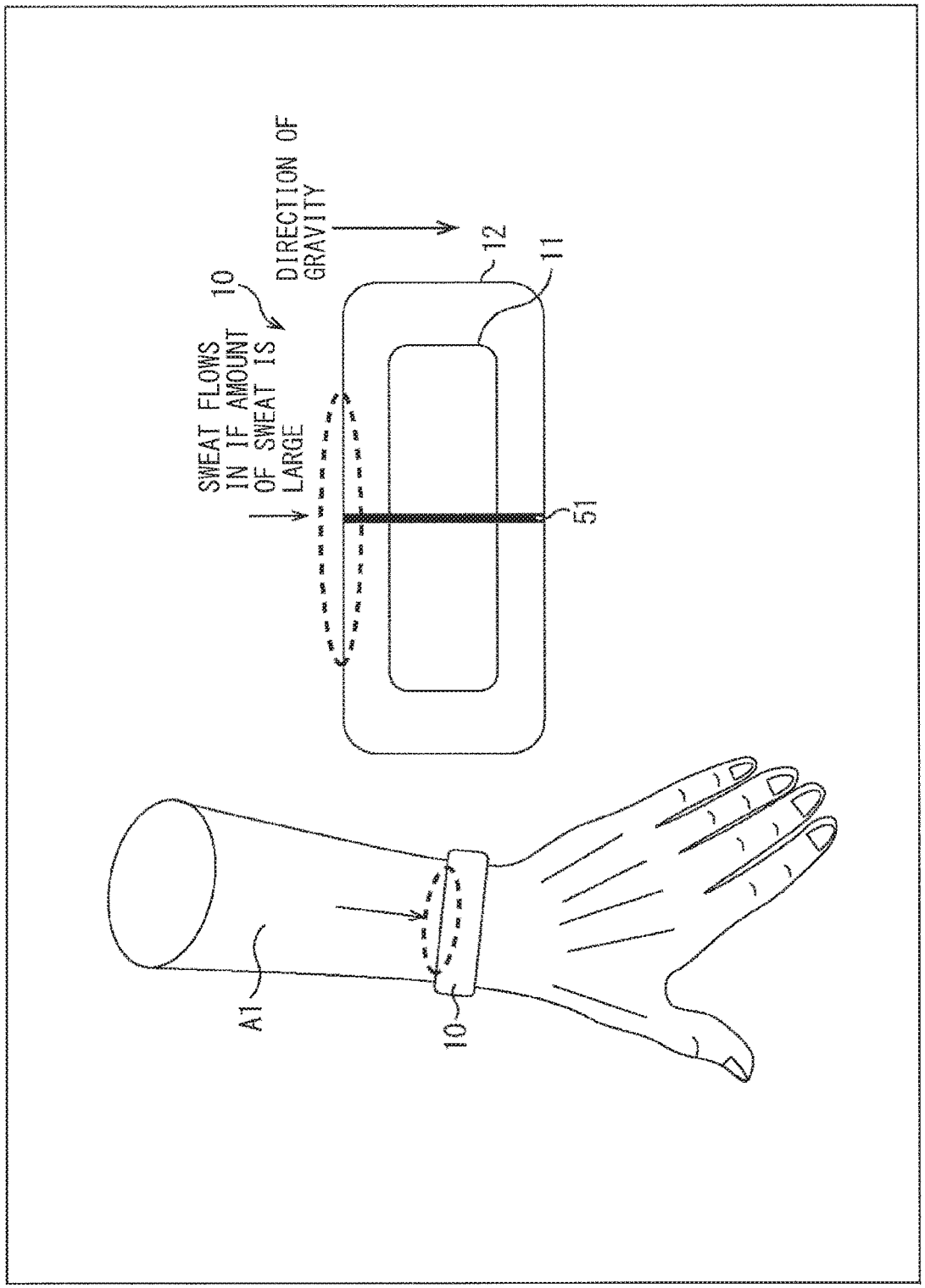
FIG. 15 is a diagram illustrating an example in a case where sweat flows into the wearable device.

For example, as illustrated in FIG. 15, in a case where the amount of sweat is large such as during physical activities or in the summer, sweat flows into in a direction toward the wearable device 10 from the upper portion of the arm A1 of the user U1. Furthermore, as a large amount of sweat flows into the groove 51 of the wearable device 10, the sweat overflows from the groove 51 on the contact surface of the device section 11, which causes the sweaty and damp condition to be more likely to occur.

Figure 16A:
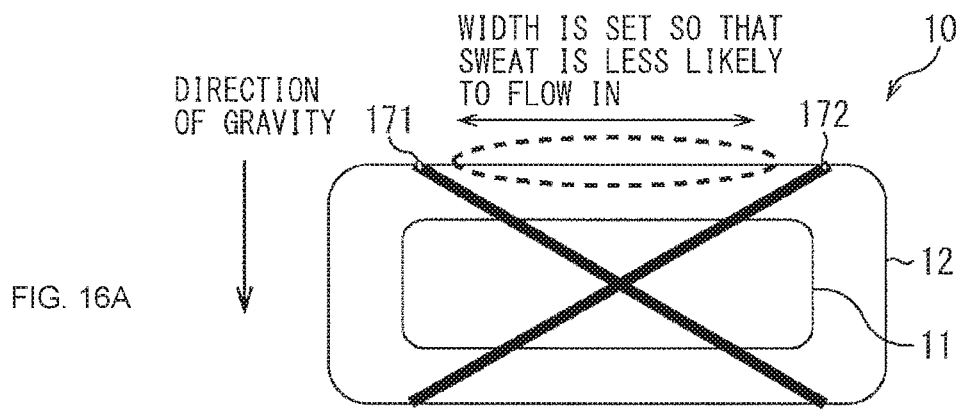
FIGS. 16A and 16B are diagrams illustrating an eighth embodiment of a groove of the wearable device.

For this case, for example, it is possible to consider that the groove is shaped as illustrated in FIG. 16A.

Specifically, a groove 171 and a groove 172 are each formed diagonally in a direction symmetrical to each other so as to cross each other at the middle in the contact surface of the device section 11, as with the groove 111 and the groove 112 in FIG. 11B.

Furthermore, the distance between an end portion of the groove 171 and an end portion of the groove 172 is set so that sweat is less likely to flow into the groove 171 and the groove 172. Thus, an ideal distance between the end portion of the groove 171 and the end portion of the groove 172 differs from an ideal distance between the end portion of the groove 111 and the end portion of the groove 112.

Figure 16B:
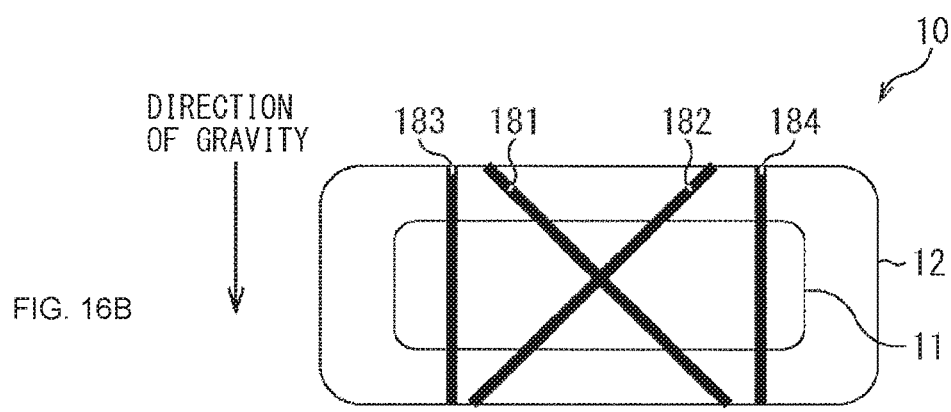

In addition, in the example illustrated in FIG. 16B, grooves are provided so that sweat is less likely to flow into the grooves. Moreover, grooves that allow sweat to flow are added.

Specifically, a groove 181 and a groove 182 are formed diagonally in a direction symmetrical to each other so as to cross each other at the middle of the contact surface of the device section 11, as with the groove 171 and the groove 172 in FIG. 16A. In addition, the width between an end portion of the groove 181 and an end portion of the groove 182 is set so that sweat is less likely to flow into the groove 181 and the groove 182, as with the distance between the end portion of the groove 171 and the end portion of the groove 172.

A groove 183 and a groove 184 are each disposed on the outer side than the groove 181 and the groove 182 in the circumferential direction, and are formed with the groove 181 and the groove 182 being disposed between the groove 183 and the groove 184. In addition, the groove 183 and the groove 184 each cross the device section 11 and the contact surface of the band 12 in the width direction.

The groove 183 is formed, for example, in a manner such that sweat traveling in a direction toward the groove 183 from the outer side (from the left side in the drawing) than the groove 183 flows into the groove 183. This makes it possible to prevent a large amount of sweat from flowing into the groove 181.

Similarly, the groove 184 is formed, for example, in a manner such that sweat traveling in a direction toward the groove 184 from the outer side (from the right in the drawing) than the groove 184 flows into the groove 184. This makes it possible to prevent a large amount of sweat from flowing into the groove 182.

Furthermore, for example, in a case where the user U1 runs as illustrated in FIG. 17A or in a case where the user U1 vertically swings his or her arm as illustrated in FIG. 17B, the posture (position and direction) of the wearable device 10 worn on the arm A1 changes as illustrated in FIG. 17C. In addition, a direction in which sweat is more likely to travel changes in relation to movement of the arm A1.

Figure 18:
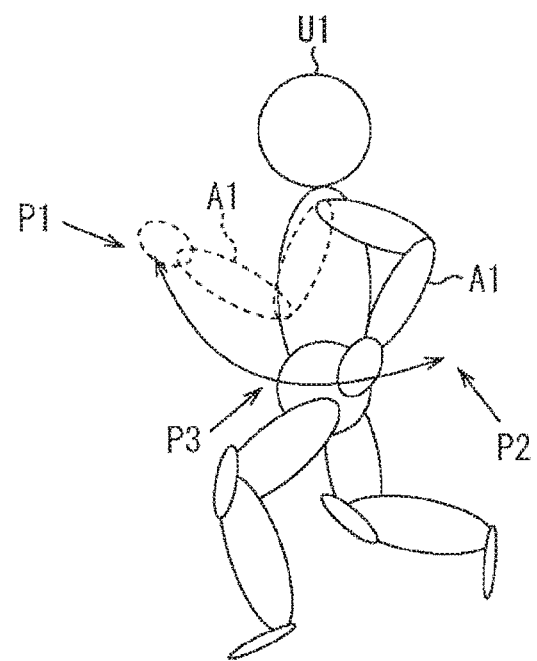
FIG. 18 is a diagram illustrating an example of a position of user's arm in a case where the user is running.

For example, in a case where the user U1 is running as illustrated in FIG. 18, the arm A1 is substantially constantly swung back and forth as indicated by the arrow. In addition, for example, the direction of sweat more likely to travel on the arm A1 differs at a position P1 where the arm A1 is at the most forward position and stops, at a position P2 where the arm A1 is at the most rearward position and stops, and at a position P3 where the arm A1 moves at the fastest speed.

Figure 19A:
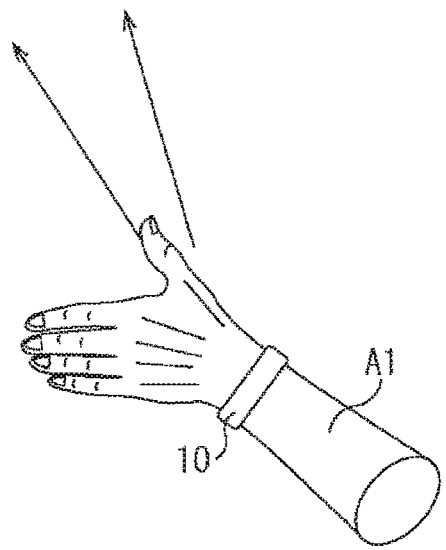
FIGS. 19A and 19B are diagrams illustrating a result of study on an appropriate groove of the wearable device in a case where a user is running.

For example, FIG. 19A illustrates an example of a direction of sweat on the arm A1 more likely to travel in a case where the arm A1 reaches the position P1 in FIG. 18. Specifically, upon the arm A1 stopping at the position P1, the sweat on the arm A1 is more likely to travel diagonally in a forward and upward direction as indicated by the arrow in the drawing, due to inertia resulting from movement of the arm A1 until then. Note that, in FIG. 19A, directions of sweat more likely to travel are indicated as a plurality of arrows due to variation among individuals.

Figure 19B:
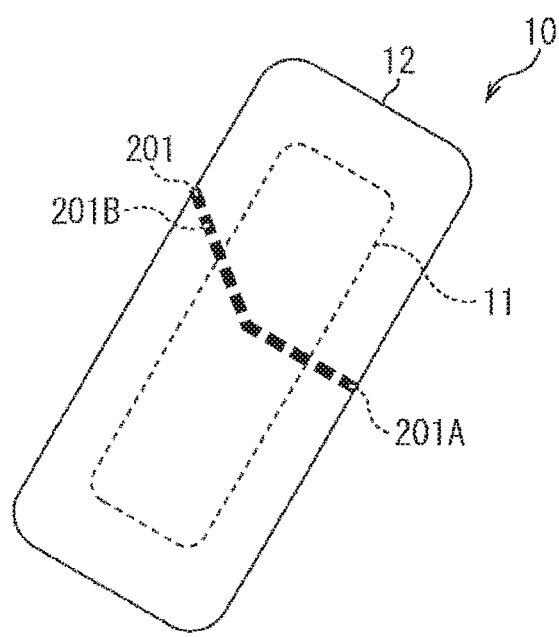

FIG. 19B illustrates an example of the groove that corresponds to movement of sweat concerning FIG. 19A. Note that, since the device section 11 is provided so as to be in contact with the arm A1 and is not able to be viewed in the direction of FIG. 19B, the positions of the device section 11 and the groove 201 are illustrated as dotted lines.

In a case where the arm A1 reaches the position in FIG. 19A, the width direction of the device section 11 is directed slightly diagonally upward and frontward as illustrated in FIG. 19B.

Furthermore, a groove 201 includes a groove 201A and a groove 201B. The groove 201A extends in the width direction from the middle of the contact surface of the device section 11 up to a side of the contact surface of the band 12 from among sides of the contact surface of the band 12 in the circumferential direction, the side being on the upper side (on a side of elbow) of the arm A1. The groove 201B extends straight from the middle of the contact surface of the device section 11 up to a side of the contact surface of the band 12 in the circumferential direction, the side being on the lower side (on a side of the back of a hand) of the arm A1. In addition, the groove 201B is diagonally sloped from the width direction toward the inner side (toward the side of a thumb) of the arm A1.

This enables sweat traveling in a direction of inertia in a case where the arm A1 stops at the position P1, to be more likely to be discharged through the groove 201.

Figure 20A:
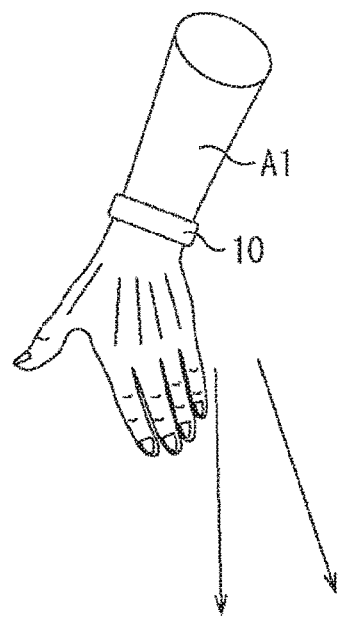
FIGS. 20A and 20B are diagrams illustrating a result of study on an appropriate groove of the wearable device in a case where a user is running.

Furthermore, FIG. 20A illustrates an example of a direction of sweat on the arm A1 more likely to travel in a case where the arm A1 reaches the position P2 in FIG. 18. Specifically, upon the arm A1 stopping at the position P2, the sweat on the arm A1 is more likely to travel downward or slightly diagonally rearward as indicated by the arrow in the drawing, due to inertia resulting from movement of the arm A1 until then. Note that, in FIG. 20A, directions of sweat more likely to travel are indicated as a plurality of arrows due to variation among individuals.

Figure 20B:
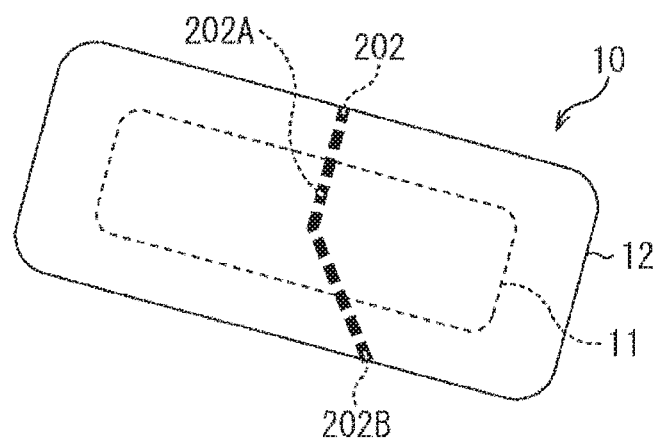

FIG. 20B illustrates an example of grooves that correspond to sweat concerning FIG. 20A. Note that, in FIG. 20B, the positions of the device section 11 and the groove 202 are illustrated as dotted lines as in FIG. 19B.

In a case where the arm A1 reaches the position in FIG. 20A, the width direction of the device section 11 are sloped substantially downward and slightly diagonally forward, as illustrated in FIG. 20B.

Furthermore, a groove 202 includes a groove 202A and a groove 202B. The groove 202A is a groove similar to the groove 201A in FIGS. 19A and 19B. The groove 202B extends straight from the middle of the contact surface of the device section 11 up to a side of the contact surface of the band 12 from among sides of the contact surface of the band 12 in the circumferential direction, the side being on the lower side (on a side of the back of a hand) of the arm A1. In addition, the groove 201B is diagonally sloped from the width direction toward the outer side (toward the side of a little finger) of the arm A1.

This enables sweat traveling in a direction of inertia in a case where the arm A1 stops at the position P2, to be more likely to be discharged to the outside through the groove 202.

Figure 21A:
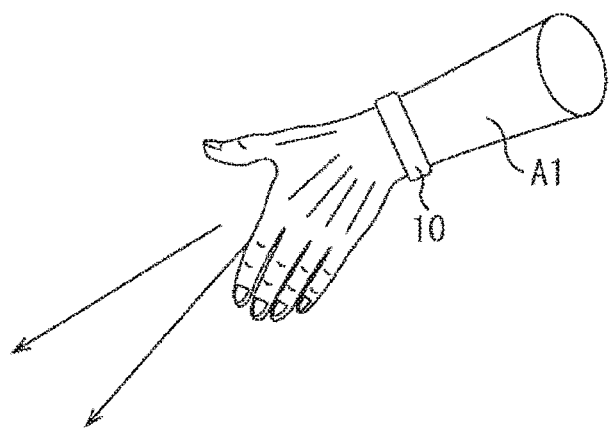
FIGS. 21A, 21B, and 21C are diagrams illustrating a result of study on an appropriate groove of the wearable device in a case where a user is running.

Furthermore, FIG. 21A illustrates an example of a direction of sweat on the arm A1 more likely to travel in a case where the arm A1 reaches the position P3 in FIG. 18. Specifically, in a case where the arm A1 moves at the fastest speed at the position P3, the sweat on the arm A1 is more likely to travel in a direction in which the arm A1 extends as illustrated by the arrow in the drawing, due to centrifugal force associated with movement of the arm A1 in the rotational direction. In addition, the direction of travel of the sweat on the arm A1 is more likely to be affected by the wind due to swing of the arm A1.

Figure 21B:
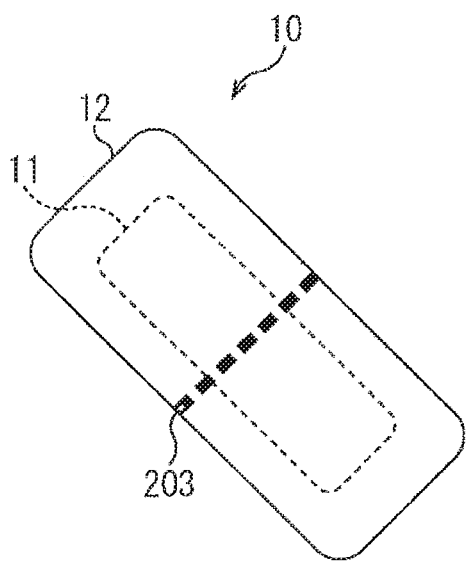

FIG. 21B illustrates an example of a groove that corresponds to movement of sweat concerning FIG. 21A. Note that, in FIG. 21B, positions of the device section 11 and a groove 203 are illustrated as dotted lines, as in FIG. 19B.

In a case where the arm A1 is disposed at the position in FIG. 21A, the width direction of the device section 11 is directed diagonally downward and forward, as illustrated in FIG. 21B.

Furthermore, the groove 203 passes through the middle of the device section 11, and crosses, in the width direction (in a direction in which the arm A1 extends), the contact surface of the device section 11 and the contact surface of the band 12, as with the groove 51 in FIG. 5.

This enables sweat traveling in a direction of centrifugal force in a case where the arm A1 moves at the fastest speed, to be more likely to be discharged to the outside through the groove 203.

Figure 21C:
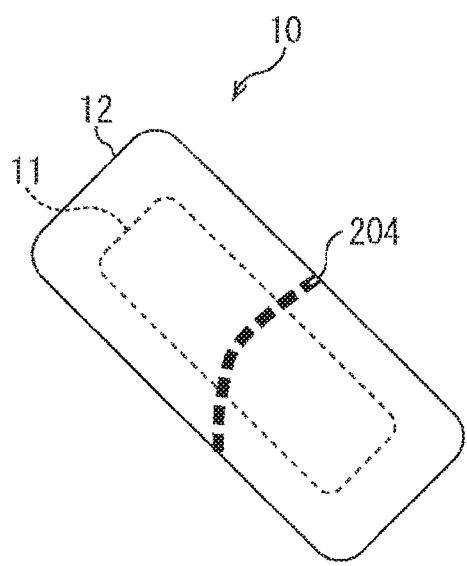

It should be noted that, instead of the groove 203, a groove 204 may be provided as illustrated in FIG. 21C on the basis of the direction of the gravity, the groove 204 having a curved shape and directed downward in a case where the arm A1 is located at the position in FIG. 21A.

Figure 22:
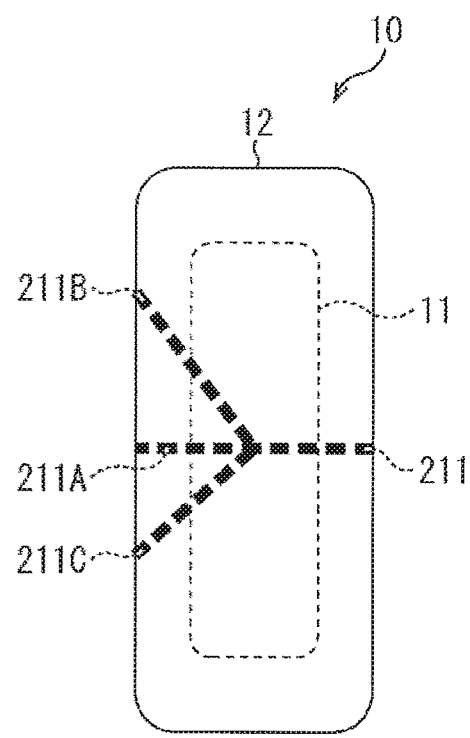
FIG. 22 is a diagram illustrating the eighth embodiment of the groove of the wearable device.

FIG. 22 illustrates an example of a final groove 211 based on a result of study in connection with FIGS. 19A, 19B, 20A, 20B, 21A, 21B, and 21C.

The groove 211 is obtained by coupling a groove 211A, a groove 211B, and a groove 211C. The groove 211A is a groove similar to the groove 203 in FIG. 21B. The groove 211B is a groove similar to the groove 201B in FIG. 19B. The groove 211C is a groove similar to the groove 202B in FIG. 20B.

This makes it possible to cause the sweat to more efficiently run away during a period of time when the user is running.

Figure 23:
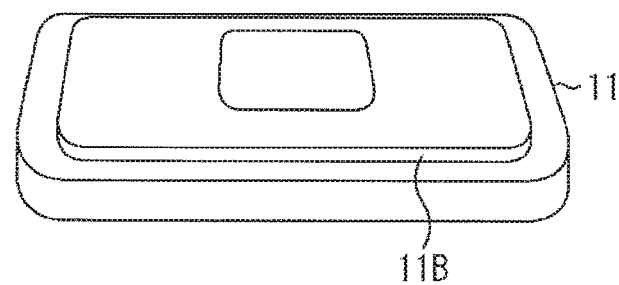
FIG. 23 is a diagram used to describe a case where the contact surface of a device section is replaceable.

It should be noted that, for example, a contact surface 11B of the device section 11 illustrated in FIG. 23 is provided so as to be able to be replaced. This allows a user to use a contact surface 11B having a groove position, direction, shape, or the like differing, for example, according to applications or situations where the wearable device 10 is worn, which makes it possible to more reliably prevent getting sweaty and damp.

<Method of Facilitating Movement of Sweat within Groove>

Next, a method of facilitating movement of sweat within a groove will be described with reference to FIGS. 24 to 26. Note that description will be made below of a case where the wearable device 10 includes the groove 111 and the groove 112 in FIG. 11B.

For example, it is assumed that sweat or moisture stays within the groove 111 and the groove 112, for example, in a case where the amount of sweat is large or the arm of a user is at rest.

Figure 24:
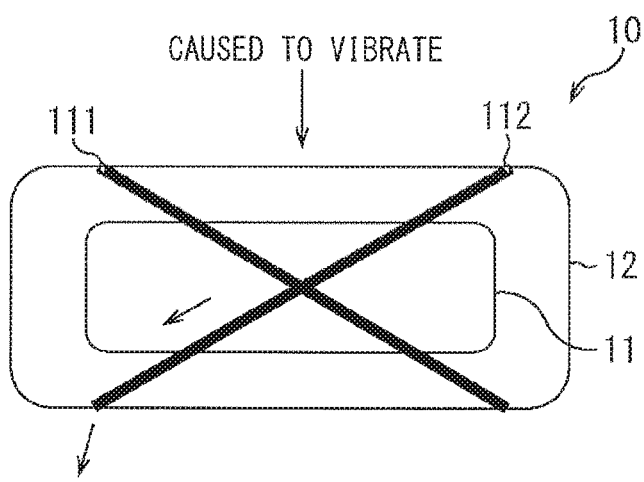
FIG. 24 is a diagram used to describe a first method of facilitating movement of sweat within a groove of the wearable device.

Furthermore, a vibrator (not illustrated) or the like built in the wearable device 10 may cause the wearable device 10 to vibrate, as illustrated, for example, in FIG. 24. This facilitates movement of the sweat or moisture within the groove 111 and the groove 112 due to the gravity and the acceleration applied to the wearable device 10 by the vibration.

Figure 25:
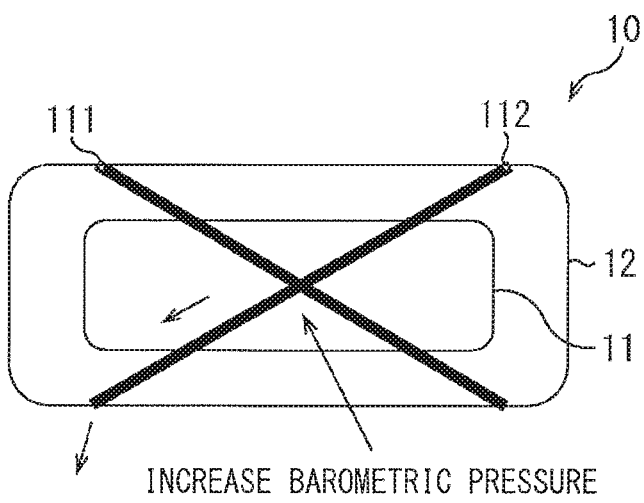
FIG. 25 is a diagram used to describe a second method of facilitating movement of sweat within a groove of the wearable device.

Furthermore, as illustrated, for example, in FIG. 25, it may be possible to facilitate the movement of the sweat or moisture within the groove 111 and the groove 112 by providing a mechanism that increases a barometric pressure on and around the intersecting portion between the groove 111 and the groove 112 to create a pressure difference within the groove 111 and the groove 112 (adjust the distribution of barometric pressure) or, delivers a wind from on and the vicinity of the intersecting portion to the outside.

An example of this mechanism that increases the barometric pressure or delivers a wind includes, for example, a wind blowing device or the like that employs, for example, supersonic vibration using ceramics to operate as an air pump. Note that the position where the barometric pressure increases or the position to which wind is delivered is changed as appropriate according to the shape of the groove or the like.

Figure 26:
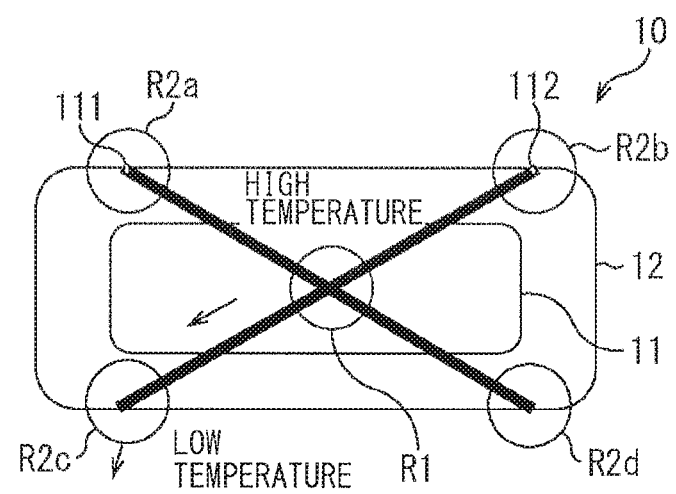
FIG. 26 is a diagram used to describe a third method of facilitating movement of sweat within a groove of the wearable device.

Furthermore, it may be possible to facilitate movement of the sweat or moisture within the groove 111 and the groove 112 by increasing temperatures of a region R1 on and around the intersecting portion between the groove 111 and the groove 112 and reducing temperatures of regions R2a to R2d on and around the end portions of the groove 111 and the groove 112 to create a temperature difference within the groove 111 and the groove 112 (adjust the distribution of temperatures), as illustrated, for example, in FIG. 26.

As for a method of achieving this temperature difference, it is considered, for example, to heat on and around the region R1 using resistance and cool on and around the regions R2a to R2d using a Peltier device. Note that the position to be heated and the position to be cooled are changed as appropriate according to the shape of the groove or the like. In addition, for example, a vent may be provided in order to easily release the heated moisture, the vent extending up to a side of the contact surface of the band 12 in the circumferential direction and on the side of the upper arm (upper side in the drawing).

2. Second Embodiment

As described above, the direction of sweat or moisture more likely to travel changes due, for example, to postures or motions of a use. In addition, an appropriate position, direction, shape or the like of the groove changes. Meanwhile, a second embodiment of the present technology dynamically changes states (position, direction, shape, or the like) of a groove or grooves in a manner determined by postures or motions of a user, or the like.

Example of Configuration of Wearable Device

Figure 27A:
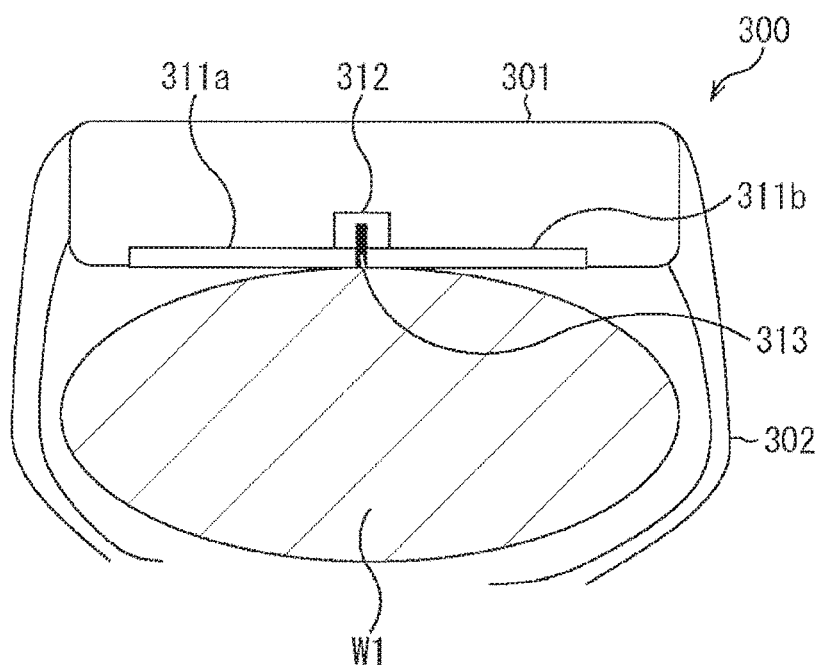
FIGS. 27A and 27B are diagrams schematically illustrating a second embodiment of a wearable device to which the present technology is applied.
Figure 27B:
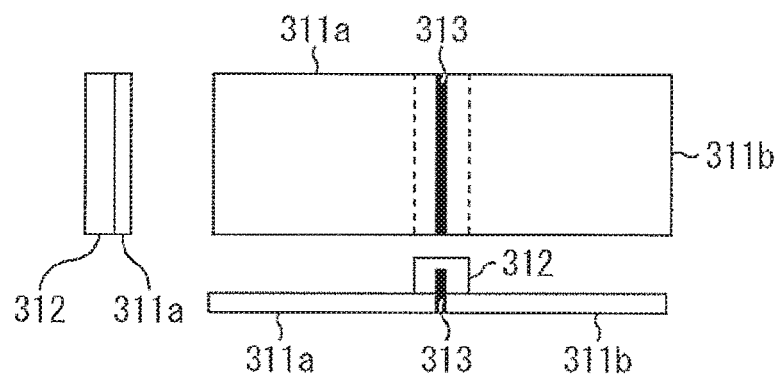

FIGS. 27A and 27B illustrate an example of a configuration of a wearable device 300 in which a state of a groove is able to dynamically change.

FIG. 27A is a schematic cross-sectional view of an example of the configuration of the wearable device 300. FIG. 27B is an orthogonal projection schematically illustrating a configuration of a contact surface of a device section 301 of the wearable device 300, the contact surface being to be brought into contact with a wrist W1 of a user.

The wearable device 300 includes the device section 301 and a band 302.

The device section 301 serves as a main body portion of the wearable device 300, and includes, therein, various types of electronic parts used to achieve functions of the wearable device 300, as with the device section 11 of the wearable device 10 described above. The body of the device section 301 includes, for example, a material similar to that of the device section 11.

The band 302 is attached to each of both ends of the device section 301 in the circumferential direction, and is a wearing unit used to wear the wearable device 300 on a wrist W1 of a user. The band 302 includes, for example, a material similar to that of the band 12 in FIGS. 1A and 1B.

The contact surface, to be in contact with the skin of the wrist W1, of the device section 301 includes a sheet 311a and a sheet 311b, each of which has a thin thickness, and has a rectangular plate shape in a normal state. For the sheet 311a and the sheet 311b, a member that is able to freely expand and contract is used. An example of the member includes a flexible rubber sheet. The sheet 311a and the sheet 311b are disposed substantially in the middle of the device section 301 in the circumferential direction with a predetermined space being provided therebetween. In addition, adjacent sides of the sheet 311a and the sheet 311b in the width direction are coupled to each other using a coupling member 312 having a shape of an inverted U in cross section. Silicon or other deformable member is used for the coupling member 312.

It should be noted that, as illustrated, for example, in FIGS. 28A and 28B FIG. 28, the sheet 311a and the sheet 311b are coupled to the coupling member 312, for example, through combination or using two-color molding.

Furthermore, a space between the sheet 311a and the sheet 311b, and a groove in the coupling member 312 form a groove 313. The groove 313 passes through the middle of the contact surface of the device section 301, and crosses, in a straight manner, the contact surface of the device section 301 in the width direction.

This groove 313 allows sweat or moisture on the wrist W1 and the contact portion of the device section 301 to be released to the outside.

<Method of Dynamically Changing State of Groove>

Furthermore, upon the sheet 311a, the sheet 311b, or both being pulled in a direction parallel to the contact surface of the device section 301, the sheet 311a and the sheet 311b are deformed in a direction parallel to the contact surface, which results in a change of a state of the groove 313.

For example, as illustrated in FIG. 29, description will be made of a case where an end portion (upper end portion in the drawing) of the sheet 311a on one side in the width direction is pulled in a parallel direction to and the circumferential direction (toward the left direction in the drawing) of the contact surface of the device section 301 as indicated by the arrow. In this case, an end portion (upper end portion in the drawing) of a side, adjacent to the groove 313, of the sheet 311b coupled to the sheet 311a through the coupling member 312 is pulled in a direction indicated by the arrow. This makes a one end (upper end portion in the drawing) of the groove 313 move in a direction indicated by the arrow. Thus, the groove 313 is sloped diagonally with respect to the width direction.

Here, an example of a method of changing a shape of the sheet 311a and the sheet 311b will be described with reference to FIGS. 30A, 30B, and 30C.

Figure 30A:
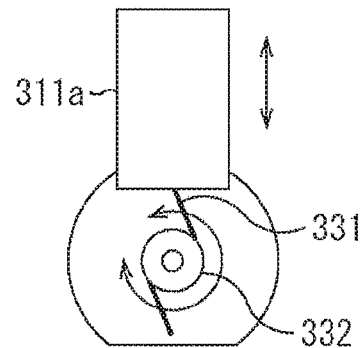
FIGS. 30A, 30B, and 30C are diagrams used to describe a method of expanding and contracting a sheet.

For example, a string 331 provided on the end portion of the sheet 311a is wound by a motor 332 and is locked to shorten the sheet 311a, as illustrated in FIG. 30A. At this time, force continuously acts on the sheet 311a in a direction toward the outside. Furthermore, upon the lock being removed, the sheet 311a is made longer due to the force acting toward the outside. At this time, a sensor or the like may be used to detect the length of the sheet 311a, and lock the motor 332 upon the sheet 311a becoming an appropriate length.

Figure 30B:
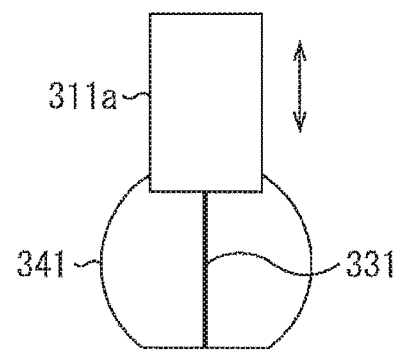

Furthermore, for example, instead of the motor 332, an actuator 341 may be used as illustrated in FIG. 30B to pull the string 331 or weaken the pulling force, thereby expanding and contracting the sheet 311a.

Figure 30C:
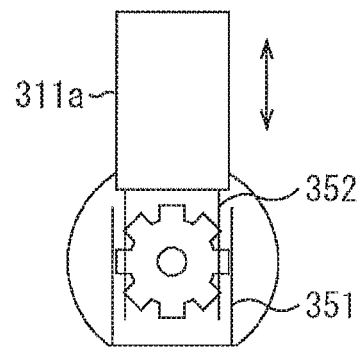

In addition, a gear 351 may be used to pull or push a string 352 to expand and contract the sheet 311a, as illustrated in the C of FIG. 30C.

It should be noted that, in a case where the sheet 311a and the sheet 311b include a rubber sheet, the sheet 311a and the sheet 311b contract in a direction perpendicular to a direction in which these sheets expand (in a direction in which they are pulled). Meanwhile, a margin may be provided for the dimensions of the sheet 311a and the sheet 311b so that no trouble occurs if they contract. In addition, the sheet 311a and the sheet 311b may be pulled so that the sheet 311a and the sheet 311b do not contract in a direction perpendicular to the direction in which the sheet 311a and the sheet 311b expand. Alternatively, design may be made such that the sheet 311a and the sheet 311b contract within a positional range where the ventilation of the groove 313 is sufficiently achieved.

In addition, for example, the sheet 311a and the sheet 311b may be configured with an artificial muscle.

Figure 31:
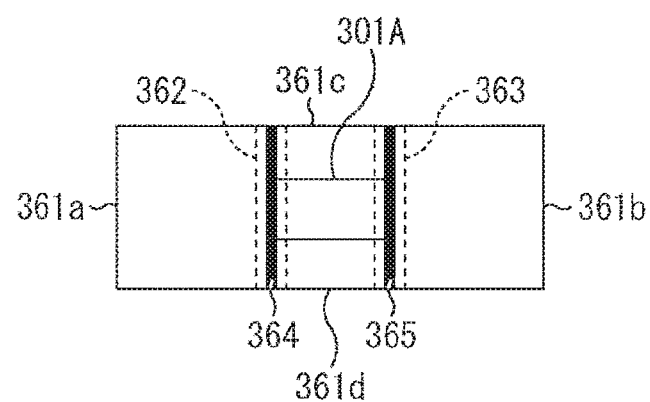
FIG. 31 is a diagram schematically illustrating a first modification example of the second embodiment of the wearable device.

FIG. 31 illustrates an example of a case where the contact surface of the device section 301 includes a raised portion 301A.

In this case, sheets 361a to 361d are disposed around the raised portion 301A on the contact surface of the device section 301. The sheets 361a to 361d include, for example, the same material as that of the sheet 311a and the sheet 311b in FIGS. 27A and 27B.

In a normal state, the sheet 361a and the sheet 361b have a rectangular shape and have an equal size. The sheet 361a is disposed at a predetermined distance from a side of each of the raised portion 301A, the sheet 361c, and the sheet 361d on one side (left side in the drawing) in the width direction. The sheet 361b is disposed at a predetermined distance from a side of each of the raised portion 301A, the sheet 361c, and the sheet 361d on the other side (right side in the drawing) in the width direction.

The sheet 361c and the sheet 361d have a rectangular shape and have an equal size in a normal state. The sheet 361c is in contact with a side of the raised portion 301A on one side (upper side in the drawing) in the circumferential direction. A side of the sheet 361c in the width direction is connected to a side of the raised portion 301A in the width direction substantially in a straight line. The sheet 361d is in contact with a side of the raised portion 301A on the other side (lower side in the drawing) in the circumferential direction. A side of the sheet 361d in the width direction is connected to a side of the raised portion 301A in the width direction substantially in a straight line.

A side of the sheet 361a on one side (right side in the drawing) in the width direction and sides of the sheet 361c and the sheet 361d on one side (left side in the drawing) in the width direction are coupled to each other with a coupling member 362 on a surface opposite to the contact surface. The coupling member 362 is a member including the same material as that of the coupling member 312 in FIGS. 27A and 27B and having substantially the same shape as that of the coupling member 312 in FIGS. 27A and 27B. Furthermore, the sheet 361a, the sheet 361c, the sheet 361d, and the coupling member 362 form a groove 364. The groove 364 is provided along a side of the raised portion 301A on one side (left side in the drawing) in the width direction so as to cross the contact surface of the device section 301 in the width direction.

A side of the sheet 361b on one side (left side in the drawing) in the width direction and sides of the sheet 361c and the sheet 361d on the other side (right side in the drawing) in the width direction are coupled to each other with a coupling member 363 on a surface opposite to the contact surface, the coupling member 363 including the same material as that of the coupling member 362, and the coupling member 363 having the same shape as that of the coupling member 362. In addition, the sheets 361b to 361d, and the coupling member 363 form a groove 365. The groove 365 is provided along a side of the raised portion 301A on the other side (right side in the drawing) in the width direction so as to cross the contact surface of the device section 301 in the width direction.

The groove 364 and the groove 365 allow sweat or moisture, for example, on the wrist W1 and the contact portion of the device section 301 to be released to the outside.

Figure 32:
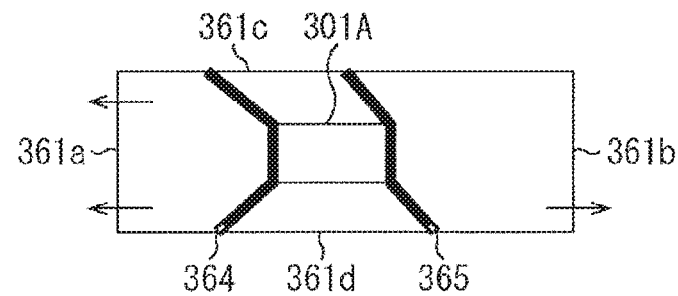
FIG. 32 is a diagram used to describe a method of changing a state of a groove.

In addition, it is possible to change states of the groove 364 and the groove 365 by pulling the sheet 361a and the sheet 361b in a direction parallel to the contact surface of the device section 301 and in the circumferential direction, as illustrated, for example, in FIG. 32.

<Another Method of Dynamically Changing State of Groove>

Next, another method of dynamically changing states of a groove will be described with reference to FIGS. 33A, 33B, 34A, 34B, 34C, 35A, 35B, 36A, 36B, 36C, 37A, 37B, 38A, 38B, 39A, and 39B.

Figure 33A:
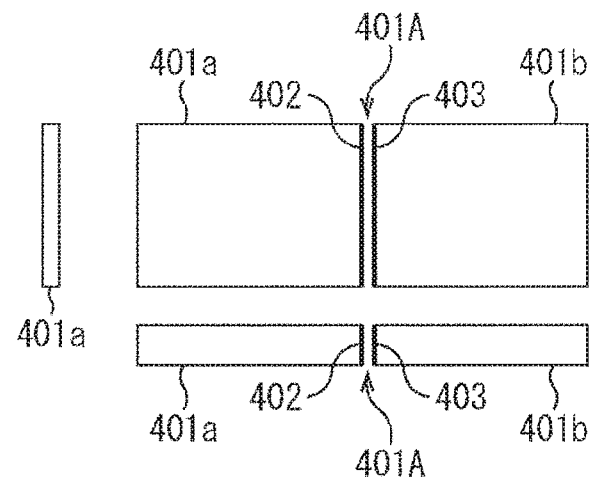
FIGS. 33A and 33B are diagrams schematically illustrating a second modification example of the second embodiment of the wearable device.

In an example in FIG. 33A, a balloon 401a and a balloon 401b are provided on the contact surface of the device section 301 in FIGS. 27A and 27B, instead of the sheet 311a, the sheet 311b, and the coupling member 312. Note that FIGS. 33A and 33B are orthogonal projections of the balloon 401a and the balloon 401b.

The balloon 401a and the balloon 401b have an equal size and have a thin plate shape in a normal state. The periphery of each of the balloon 401a and the balloon 401b includes a rubber. The balloon 401a and the balloon 401b are hollow members. The balloon 401a and the balloon 401b are arranged in the circumferential direction with a predetermined space being given therebetween. In addition, a wall 402 and a wall 403 including metal and used to maintain the shape are formed on opposing surfaces of side surfaces of the balloon 401a and the balloon 401b. In addition, a space between the wall 402 and the wall 403 forms a groove 401A.

It is possible to cause the balloon 401a and the balloon 401b to inflate and shrink in a direction parallel to the contact surface of the device section 301 by adjusting the amount of air therein. Furthermore, as the balloon 401a inflates or shrinks, an end portion of the wall 402 on one side in the width direction moves in the circumferential direction. Similarly, as the balloon 401b inflates or shrinks, an end portion of the wall 403 on one side in the width direction moves in the circumferential direction.

Figure 33B:
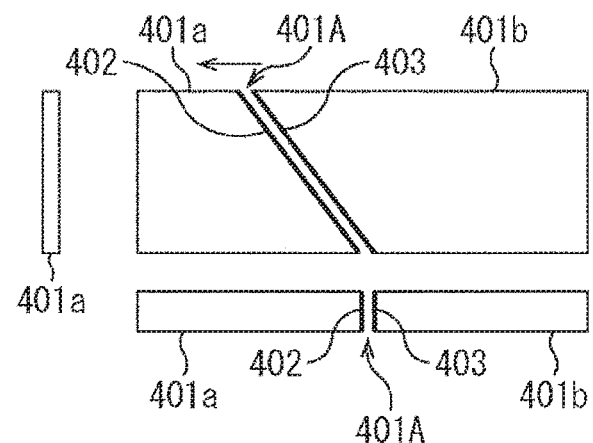

As illustrated, for example, in FIG. 33B, the balloon 401a is caused to shrink to cause the end portion of the wall 402 on one side (upper side in the drawing) to move in the circumferential direction (left direction in the drawing). In addition, the balloon 401b is caused to inflate to cause the end portion of the wall 403 on one side (upper side in the drawing) to move in the circumferential direction (left direction in the drawing). This enables an end portion, on one side (upper side in the drawing), of the groove 401A between the wall 402 and the wall 403 to move in the circumferential direction (left direction in the drawing) to cause the groove 401A to lean with respect to the width direction.

Here, a method of changing shapes of the balloon 401a and the balloon 401b through inflation or shrinking will be described with reference to FIGS. 34A 34B, 34C, 35A, 35B, 36A, 36B, 36C, 37A, 37B, 38A, and 38B.

Figure 34B:
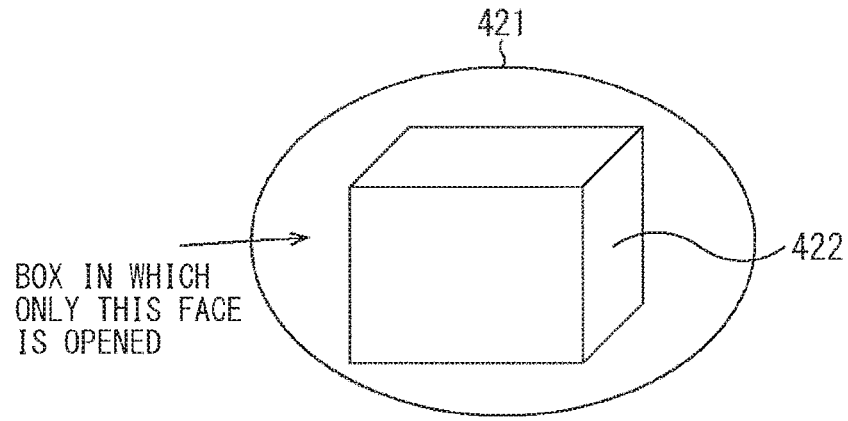
Figure 34B:
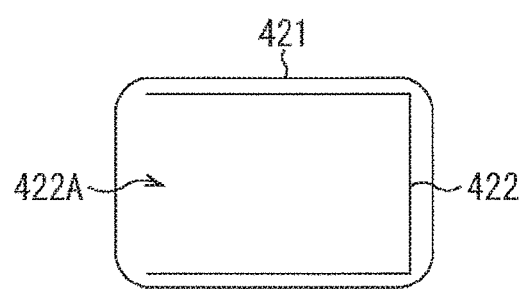
Figure 34C:
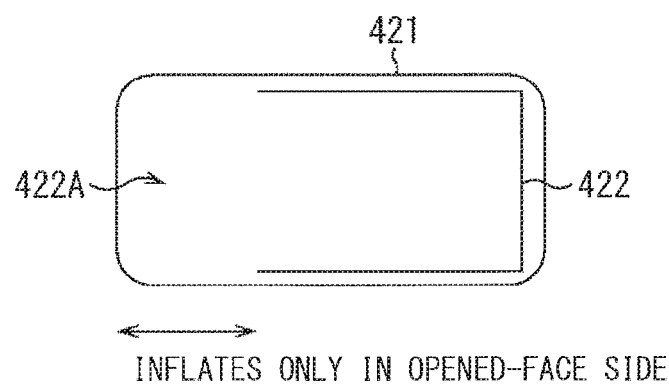

For example, a balloon 421 is put on a box 422 having one face (face 422A on the left side in FIG. 34B) opened as illustrated in FIGS. 34A and FIG. 34B. Note that, in FIG. 34A, illustration is given in a manner such that a space is provided between the balloon 421 and the box 422. Actually, however, the balloon 421 is put on the box 422 so as to be in close contact with the periphery of the box 422 as illustrated in FIG. 34B.

Here, for example, upon air being supplied within the box 422, barometric pressure rises within the box 422. Furthermore, the volume of the balloon 421 increases so as to maintain the barometric pressure within the box 422 to be constant. At this time, air moves toward the opened face 422A of the box 422. Thus, it is possible to make the balloon 421 inflate only in a direction of the opened face 422A of the box 422.

Figure 35A:
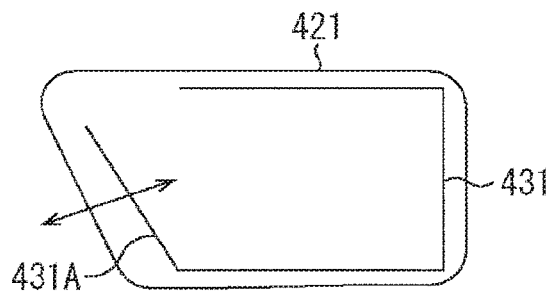
FIGS. 35A and 35B are diagrams used to describe a method of changing a shape of a balloon.

Furthermore, for example, a door 431A may be provided on the opened face of the box 431 as illustrated in FIG. 35A. In addition, the wall 402 and the wall 403 in FIGS. 33A and 33B are configured with the door 431A. Moreover, the door 431A is opened or closed through inflation and shrinking of air within the balloon 421, which makes it possible to control a state of the groove 401A.

Figure 35B:
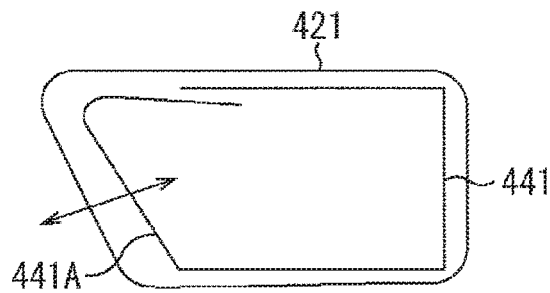

In addition, for example, as with a door 441A of a box 441 in FIG. 35B, it is possible to make the groove 401A into a curved shape by changing the shape of the door 441A.

Here, an example of a method of controlling the door 441A of the box 441 in FIG. 35B will be described with reference to FIGS. 36A, 36B, and 36C.

Figure 36A:
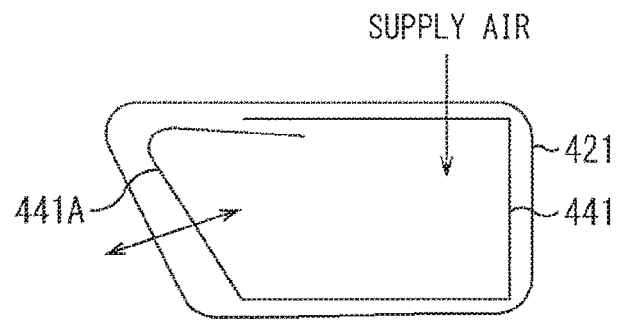
FIGS. 36A, 36B, and 36C are diagrams used to describe a method of changing a shape of a balloon.

For example, air is supplied into the box 441 from the outside using a small blower (not illustrated) or the like, or air within the box 441 is discharged using a discharging blower (not illustrated) or the like, to adjust the amount of air within the box 441, as illustrated in FIG. 36A. This makes it possible to control the position or the shape of the door 441A.

Figure 36B:
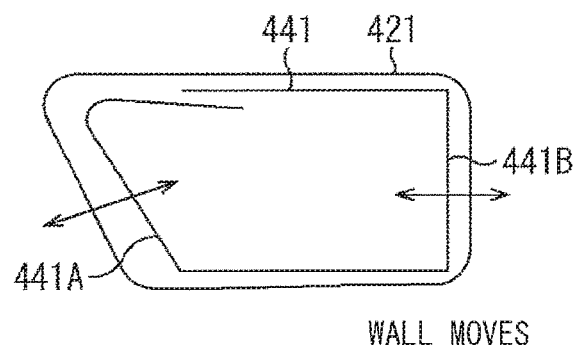

Furthermore, for example, as illustrated in FIG. 36B, a wall 441B opposed to the door 441A of the box 441 is configured so as to be able to perform parallel movement in a direction toward the door 441A or in a direction away from the door 441A using an actuator or the like. In addition, the wall 441B is parallel moved and the volume within the box 441 is increased/decreased, which makes it possible to control the position or the shape of the door 441A.

Figure 36C:
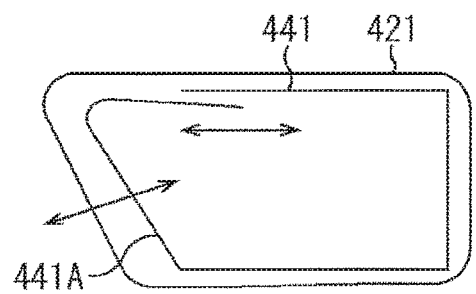

Moreover, for example, force may be applied to an unfixed end portion of the door 441A using a small actuator or the like to move the door 441A or change the shape of the door 441A as illustrated in FIG. 36C. In this case, airtightness of the balloon 421 is not so important.

It should be noted that it is desirable that the wall 402 and the wall 403 in FIGS. 33A and 33B be moved in association with each other so that the width of the groove 401A is maintained substantially at constant. That is, it is desirable that the wall 402 and the wall 403 constantly move by the same amount in the same direction.

Figure 37A:
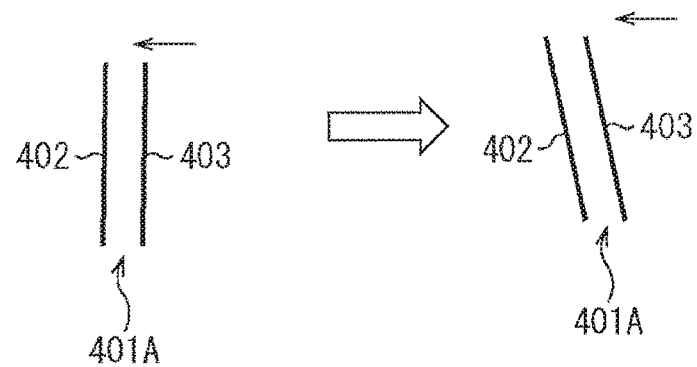
FIGS. 37A and 37B are diagrams used to describe a method of changing a state of a groove.

In particular, in a case where one wall from among the wall 402 and the wall 403 moves toward the other wall, it is desirable that the other wall move in a manner similar to the one wall. For example, as illustrated in FIG. 37A, in a case where an end portion of the wall 403 on one side (upper side in the drawing) moves in a left direction (a direction toward the wall 402) as indicated by the arrow, it is desirable that an end portion of the wall 402 on one side (upper side in the drawing) be also moved in a left direction (direction away from the wall 403). This makes it possible to prevent the ventilation from deteriorating due to the groove 401A being narrowed.

Figure 37B:
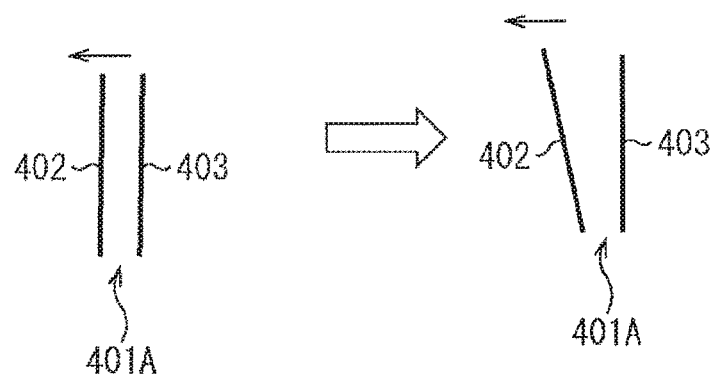

On the other hand, in a case where one wall from among the wall 402 and the wall 403 moves in a direction away from the other wall, the other wall does not necessarily have to be moved in association with the one wall. For example, as illustrated in FIG. 37B, in a case where an end portion of the wall 402 on one side (upper side in the drawing) moves in a left direction (direction away from the wall 403) as indicated by the arrow, the wall 403 does not necessarily have to be moved. This results in the width of the groove 401A being widened as illustrated in the diagram on the right side in FIG. 37B. This, however, does not adversely affect the ventilation.

Next, an example of a method of changing shapes of the balloon 401a and the balloon 401b in a linked manner will be described with reference to FIGS. 38A and 38B.

Figure 38A:
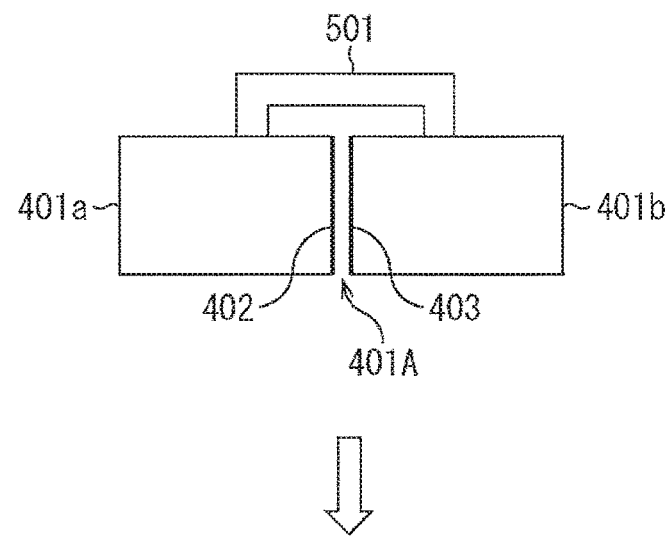
FIGS. 38A and 38B are diagrams used to describe a method of changing a shape of a balloon.
Figure 38B:
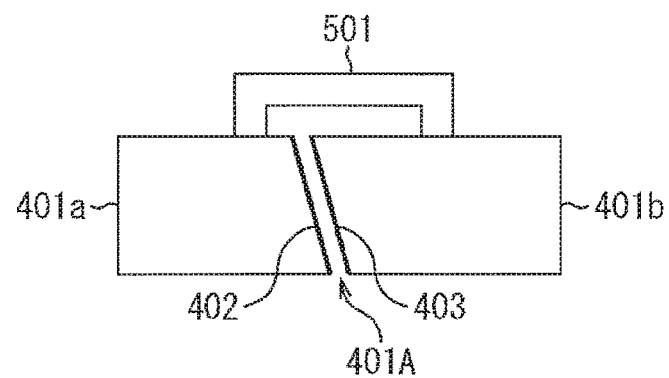

For example, as illustrated in FIG. 38A, the balloon 401a and the balloon 401b are coupled to each other using a pipe 501. This allows air to flow between the balloon 401a and the balloon 401b through the pipe 501. With this configuration, for example, if the barometric pressure of either one of the balloon 401a and the balloon 401b is varied to change the shape thereof, air travels between the balloons through the pipe 501 so as to keep the sum total of volumes of the two balloons constant and cancel out variation in barometric pressure. This allows the shape of one of the two balloons to change in a manner that associates with the change of the shape of the other balloon. This makes it possible to change the shape of the other balloon in association with change of the shape of the one balloon.

Figure 39A:
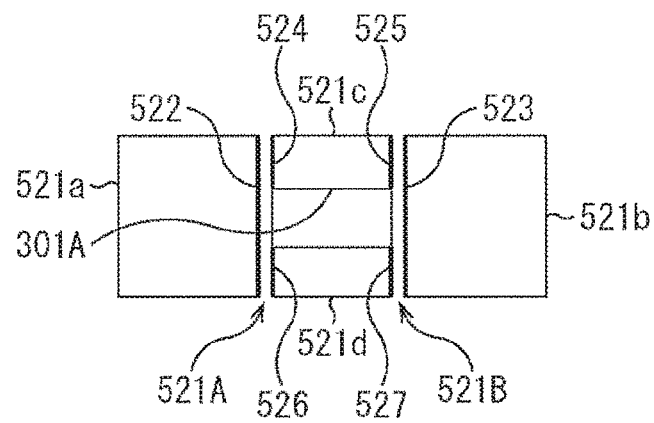
FIGS. 39A and 39B are diagrams schematically illustrating a third modification example of the second embodiment of the wearable device.
Figure 39B:
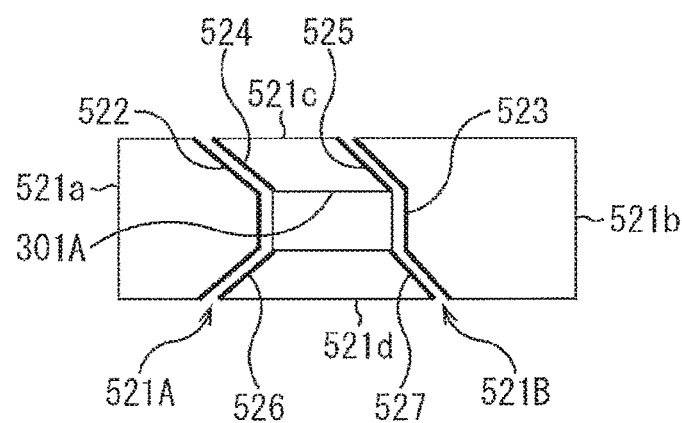

FIGS. 39A and 39B illustrate an example of a case where a raised portion 301A is provided on the contact surface of the device section 301.

In this case, balloons 521a to 521d are disposed around the raised portion 301A on the contact surface of the device section 301. The balloons 521a to 521d include, for example, the same material as that of the balloon 401a and the balloon 401b in FIGS. 33A and 33B.

The balloon 521a and the balloon 521b include thin, hollow members having a rectangular, plate shape and having the same size in a normal state. The balloon 521a is disposed at a predetermined distance from a side of each of the raised portion 301A, the balloon 521c, and the balloon 521d on one side (left side in the drawing) in the width direction. A wall 522 is provided on a side surface of the balloon 521a, the side surface being opposed to a side surface of the raised portion 301A. The balloon 521b is disposed at a predetermined distance from a side of each of the raised portion 301A, the balloon 521c, and the balloon 521d on the other side (right side in the drawing) in the width direction. A wall 523 is provided on a side surface of the balloon 521b, the side surface being opposed to a side surface of the raised portion 301A.

The balloon 521c and the balloon 521d include thin, hollow members having a rectangular shape and having the same size in a normal state. The balloon 521c is in contact with a side of the raised portion 301A on one side (upper side in the drawing) in the circumferential direction. A side of the balloon 521c in the width direction is connected to a side of the raised portion 301A in the width direction substantially in a straight line. A wall 524 is provided on a side surface of the balloon 521c, the side surface being opposed to the wall 522. A wall 525 is provided on a side surface of the balloon 521c, the side surface being opposed to the wall 523. The balloon 521d is in contact with a side of the raised portion 301A on the other side (lower side in the drawing) in the circumferential direction. A side of the balloon 521d in the width direction is connected to a side of the raised portion 301A in the width direction substantially in a straight line. A wall 526 is provided on a side surface of the balloon 521d, the side surface being opposed to the wall 523. A wall 527 is provided on a side surface of the balloon 521d, the side surface being opposed to the wall 523.

It should be noted that the walls 522 to 527 include, for example, a material similar to that of the wall 402 and the wall 403 in FIGS. 33A and 33B.

A space between the wall 522 and side surfaces of the wall 524, the wall 526, and the raised portion 301A on one side (left side in the drawing) forms a groove 521A. A space between the wall 523 and side walls of the wall 525, the wall 527, and the raised portion 301A on the other side (right side in the drawing) forms a groove 521B.

Figure 40:
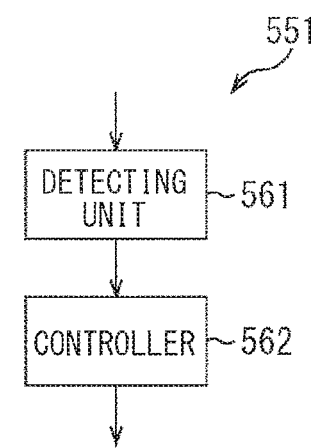
FIG. 40 is a block diagram illustrating an example of a configuration of an information processing unit.

Furthermore, for example, the balloons 521a to 521d are caused to inflate or shrink in a direction parallel to the contact surface of the device section 301 to change the shape thereof, as illustrated in FIG. 39B. This makes it possible to change states of the groove 521A and the groove 521B Example of Configuration of Information Processing Unit FIG. 40 illustrates an example of a configuration of an information processing unit 551 that performs control to facilitate movement of sweat within a groove as described with reference to FIGS. 24 to 26, or change a state of a groove as described with reference to FIGS. 27A, 27B, 28A, 28B, 29, 30A, 30B, 30C, 31, 32, 33A, 33B, 34A, 34B, 34C, 35A, 35B, 36A, 36B, 36C, 37A, 37B, 38A, 38B, 39A, and 39B.

The information processing unit 551 is achieved, for example, with a processor built in the device section 11 or the device section 301 and performing a predetermined control program. The information processing unit 551 includes a detecting unit 561 and a controller 562.

The detecting unit 561 detects, for example, states of the wearable device 10 or the wearable device 300, states (for example, states of a portion where the wearable device 10 or the wearable device 300 is worn) of a user, and the like, on the basis of sensor data from various types of sensors built in the device section 11 or the device section 301. For example, the detecting unit 561 detects a state of a physical activity at a wearing portion, the amount of or the viscosity of sweat at a wearing portion (or a contact portion), or the like. The detecting unit 561 supplies the controller 562 with a detection result.

The controller 561 performs control, for example, to facilitate movement of sweat within the groove or adjust a state of a groove, on the basis of the detection result by the detecting unit 561. For example, the controller 561 causes the wearable device 10 to vibrate or controls a barometric pressure or temperatures within a groove of the wearable device 10 on the basis of the amount of or the viscosity of sweat at a wearing portion (or a contact portion), thereby facilitating movement of the sweat within the groove. In addition, for example, the controller 561 controls shapes of the sheet 311a and the sheet 311b (FIGS. 27A and 27B) or shapes of the balloon 401a and the balloon 401b (FIGS. 33A and 33B) so that the state of the groove fits a state of a physical activity at the wearing portion.

Here, with reference to FIGS. 41A, 41B, and 42, description will be made of an example of a case where the detecting unit 561 detects, as a state of a user, a state of an arm on which the wearable device 300 is worn.

Here, with reference to FIGS. 41 and 42, description will be made of an example of a case where the detecting unit 561 detects, as a state of a user, a state of an arm on which the wearable device 300 is worn.

For example, the detecting unit 561 detects a state of the arm of the user, on the basis of a detection result by a three-dimensional acceleration sensor (not illustrated) concerning an x-axis, a y-axis, and a z-axis and built in the device section 301 of the wearable device 300, and information regarding which arm of the user the wearable device 300 is worn on.

Figure 41A:
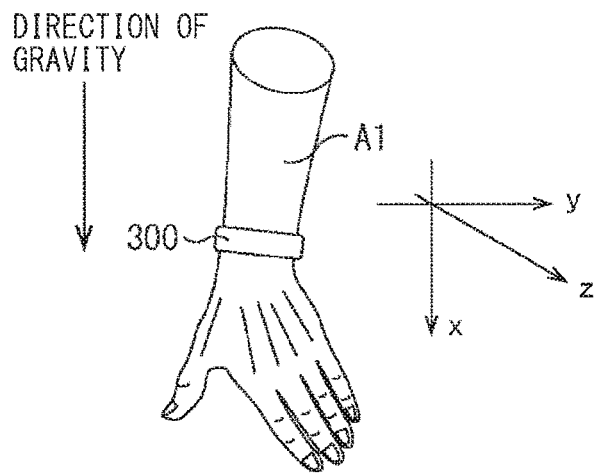
FIGS. 41A and 41B are diagrams used to describe a method of detecting a state of an arm.
Figure 41B:
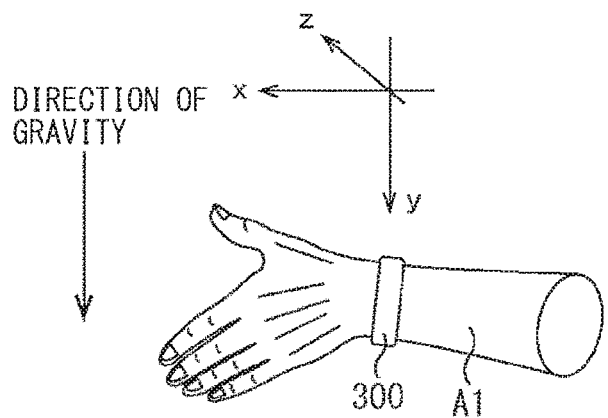
Figure 42:
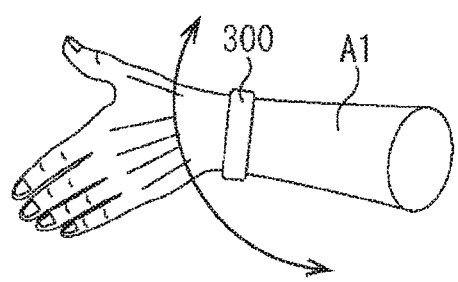
FIG. 42 is a diagram used to describe a method of detecting a state of an arm.

For example, in a case where the detection result concerning the posture of an arm A1 and made by an acceleration sensor is indicated using a coordinate axis on the right side in FIG. 41A, the detecting unit 561 determines that the user is in a state where the arm A1 is lowered. In addition, in a case where the detection result concerning the posture of the arm A1 and made by the acceleration sensor is indicated using a coordinate axis on the right side in FIG. 41B, the detecting unit 561 determines that the user is in a state where the arm A1 is extended forward.

Furthermore, for example, the detecting unit 561 carries out an integration of accelerations in three axial directions detected by acceleration sensors to detect a traveling speed of the arm A1, which makes it possible to detect a motion of the arm A1. In addition, for example, the detecting unit 561 is able to estimate an action of the user on the basis of a motion of the arm A1. For example, in a case where the arm A1 swings back and forth in a regular manner, the detecting unit 561 estimates that the user is running.

It should be noted that the state of the user may be detected using any method other than the methods described above. For example, it is possible to detect the state of a user on the basis of an image captured using a camera. In addition, for example, in a case where a marker configured by an LED or the like is provided on the wearable device 10 or the wearable device 300, it is possible to detect the state of a user by following movement of the marker.

Furthermore, at the time of facilitating movement of sweat within a groove of the wearable device 10 or the wearable device 300 or adjusting a state of a groove, noise may be produced in a sensor built in the device section 11 or the device section 301 due to vibration or the like.

Figure 43:
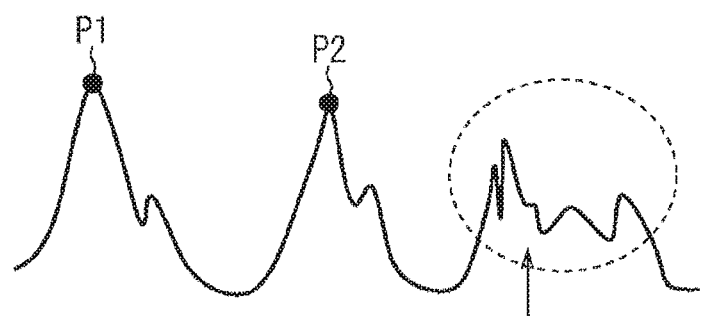
FIG. 43 is a diagram illustrating an example of a detected waveform of a pulse wave.

For example, FIG. 43 illustrates an example of a waveform of sensor data from a pulse wave sensor built in the device section 11 or the device section 301 and using photoplethysmography (PPG). For example, at the time of facilitating movement of sweat within a groove or adjusting a state of the groove, noise may occur in sensor data as indicated in the region of a dotted line in the drawing. Thus, in a case of calculating a heart rate on the basis of a peak in sensor data from the pulse wave sensor, it is desirable to calculate the heart rate on the basis of the peak P1, the peak P2, and the like without using data within the region of the dotted line.

3. Modification Examples

Below, modification examples of embodiments of the present technology described above will be described.

Example Concerning Range of Application of Present Technology

The description above gives an example in which the present technology is applied to a wearable device worn on a wrist of a user. However, the present technology is able to be applied to various types of wearable devices worn on portions other than a wrist.

Figure 44:
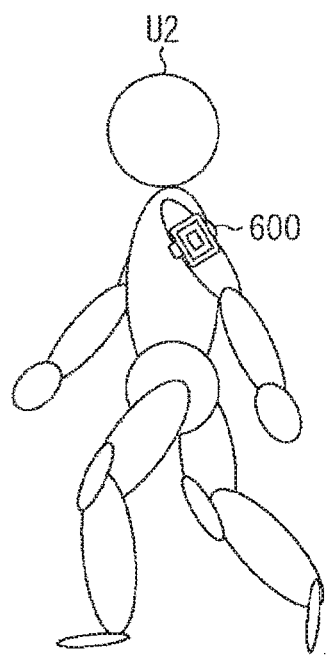
FIG. 44 is a schematic view of an example in which a third embodiment of the wearable device is worn, the wearable device being a device to which the present technology is applied.
Figure 45:
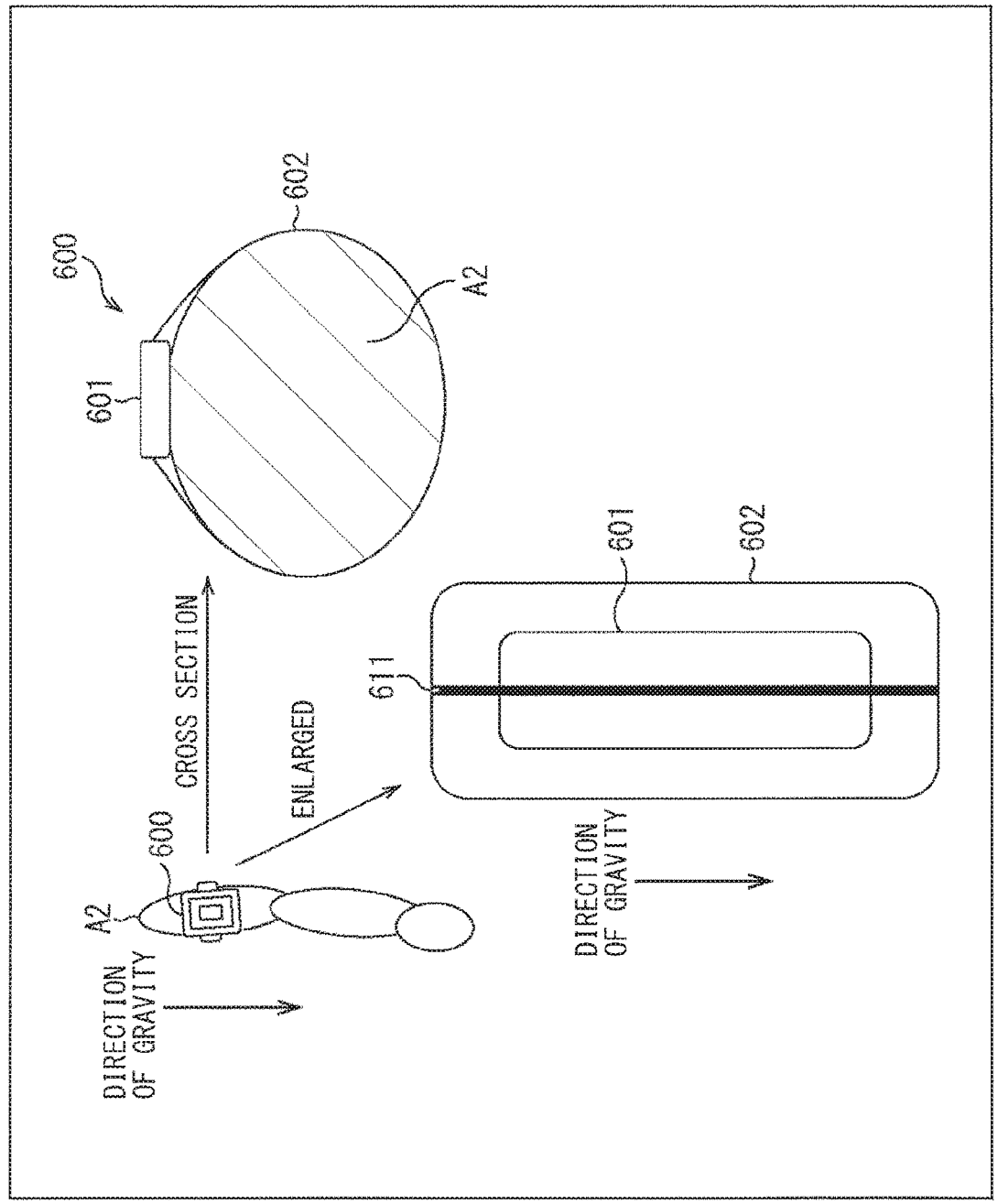
FIG. 45 is a schematic view of an example of a configuration of the third embodiment of the wearable device to which the present technology is applied.

For example, as illustrated in FIGS. 44 and 45, the present technology is able to be applied to a wearable device 600 worn on an upper arm of an arm A2 of a user U2.

The wearable device 600 includes a device section 601 and a band 602.

The device section 601 serves as a main body portion of the wearable device 600. As with the device section 11 of the wearable device 10 described above, the device section 601 includes, therein, various electronic parts used to achieve functions of the wearable device 600. The device section 601 includes a body including, for example, a material similar to that of the device section 11.

The band 602 is attached to each of both ends of the device section 601 in the circumferential direction, and is a wearing unit used to wear the wearable device 600 on an arm portion of a user. The band 602 includes, for example, silicon or rubber that follows movement of muscle.

Figure 46:
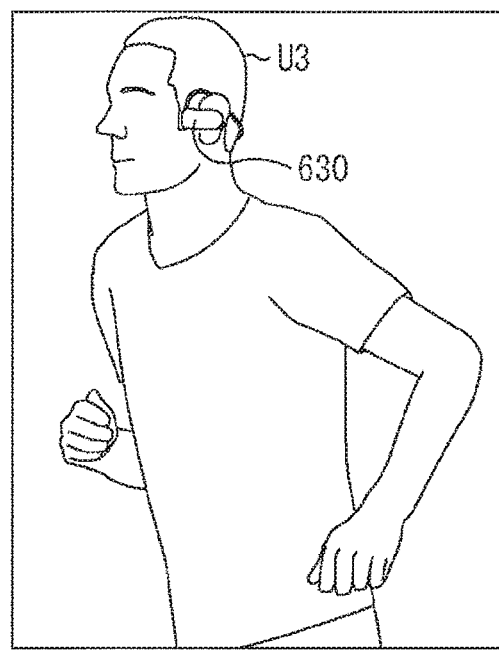
FIG. 46 is a schematic view of another example of the wearable device.

It should be noted that, as compared with a wrist, an upper arm portion of a person typically has a round shape, and has a larger curvature in the circumferential direction. Thus, in order to increase area of a contact surface of the device section 601 that is brought into contact with a skin of a user, it is desirable that the device section 601 be elongated in a direction in which the arm A2 extends, for example, as illustrated in FIG. 46. In this case, in a state where the wearable device 600 is worn on the arm A2 and the arm A2 is lowered, the longitudinal direction of the device section 601 substantially matches the direction of the gravity.

Thus, unlike the wearable device 10 in FIG. 5, the wearable device 600 includes a groove 611 provided in the longitudinal direction of the device section 601. That is, the groove 611 is provided so as to pass through the middle of the contact surface of the device section 601 and cross the contact surface of the device section 601 and the contact surface of the band 602 in the width direction. This makes it possible to cause sweat and moisture to efficiently run away from the contact portion between the wearable device 600 and the arm A2.

It should be noted that, for example, a groove that deals with sweat flowing into the wearable device 600 from the upper portion of the arm A2 may be provided in a manner similar to the example described above with reference to FIGS. 16A and 16B.

Figure 47:
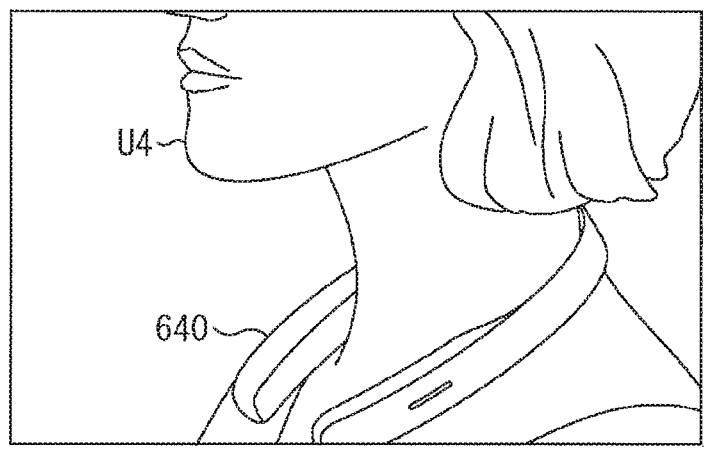
FIG. 47 is a schematic view of another example of the wearable device.

Furthermore, for example, it is possible to apply the present technology to an earphone type wearable device 630 to be worn on a head portion of a user U3 in FIG. 46, or a neckband type wearable device 640 to be worn on a neck of a user U4 in FIG. 47.

Still furthermore, it is possible to apply the present technology to other types than those described above, and it is also possible to apply the present technology, for example, to wearable devices of various types such as an eyeglasses type, a watch type, a bracelet type, a neckless type, a headset type, or a head-mount type.

Still furthermore, it is also possible to apply the present technology to a wearable device worn on other portions of a user than those described above, such as a chest, a belly, a back, a waist, or a leg.

Still furthermore, in addition to applying to a wearable device, it is also possible to apply the present technology to various types of information processing device having a contact surface to be in contact with a skin of a user. In this case, a contact surface of the information processing device includes, for example, a ventilating groove that crosses the contact surface.

Modification Example Concerning Specifications of Groove

As described above, it is possible to change the number, the position, the direction, the shape, and the like of grooves as appropriate, on the basis of the shapes of the contact surfaces of the main body portion (device section) and the contact portion (band), a portion of a user to be brought into contact with the contact surface, the position and direction of the contact surface with respect to the portion, a motion of the portion, a direction of force at the portion, and the like.

For example, the example described above provides an example in which the width and the depth, serving as a factor of the shape of a groove, are set to be 3 mm. However, it is possible to set the width or depth of a groove to be any given value. In addition, for example, the width or depth of the groove may be changed at a halfway point.

However, it is desirable to set the width or depth of a groove so that the skin of a person does not enter the groove. Such a width or depth of a groove varies according to the hardness (for example, bone, muscle, fat, or the like) of a portion where the wearable device is worn, or the like.

Furthermore, it is possible for the groove to have a shape other than a straight line.

Modification Example Concerning Control of State of Groove

For example, a state (position, direction, shape, or the like) of a groove may dynamically change according to user's constitution or physical condition. Here, user's constitution or physical condition includes, for example, the amount of sweat, the thickness of a wearing portion, the amount of body hair at the wearing portion, body temperatures, and the like.

Furthermore, for example, a state of a groove may dynamically change according to a state where the wearable device is worn, or a state of the wearing portion. Here, the state where the wearable device is worn includes, for example, the degree of tightness to the wearing portion, and the like. The state of the wearing portion includes, for example, the distance of move of the wearing portion, the speed (for example, a way of swinging an arm), and the like.

It should be noted that, for example, in a case where information regarding user's constitution, physical condition, physical activities to be carried out, or the like is acquired or learned in advance, the controller 562 (FIG. 40) may estimate in advance a state of a groove that is highly likely to be used, on the basis of the information. In addition, the controller 562 may set, in advance, the state of a groove to be an estimated state, or give high priority to the estimated state at the time of adjusting the state of the groove.

Furthermore, for example, by estimating a period of time until the amount of sweat of a user increases during a physical activity, a state of a groove may be changed before the amount of sweat increases. This makes it possible to reduce the frequency of changing the state of a groove during a physical activity, or avoid making a user feel discomfort. Note that the period of time until the user increases the amount of sweat may be estimated using data (for example, statistical values or the like) concerning another user.

Other Modification Example

For example, in a case where no improvement in a state of being sweaty and damp is able to be detected on the basis of a detection result by a sweat sensor or the like, the controller 562 (FIG. 40) may, for example, loosen a wearing unit (band) to reduce the degree of contact of the wearable device with a skin of a user. At this time, in a case where sensor data from a sensor built in the device section fluctuate due to the loosening of the band, it is desirable to correct the sensor data as appropriate.

It should be noted that the corrected sensor data are highly likely to have deteriorated accuracy. Thus, information indicating that the sensor data have been corrected may be added in a manner that can give an idea that the sensor data have reduced reliability. This makes it possible to perform processing of increasing the reliability of the sensor data, or notify that the reliability is low, at the time of using the corrected sensor data.

Alternatively, in a case where no improvement in a state of being sweaty and damp is detected, the controller 562 may notify a user to wipe the sweat.

Furthermore, the vicinity of the contact surface of the main body portion (device section) of the wearable device does not necessarily have to be surrounded by the contact surface of the wearing unit (band). In a case where the vicinity of the contact surface of the main body portion is not surrounded by the contact surface of the wearing unit, a ventilating groove is provided only on the contact surface of the main body portion, for example.

4. Others

Embodiments according to the present technology are not limited to the embodiments described above. Various modifications are possible within the scope of the main point of the present technology.

Furthermore, it is possible for the present technology to have configurations described below.

(1)

An information processing device to be worn by a user, the information processing device including:
- a main body portion having a first contact surface that is brought into contact with a skin of the user; and
- a groove that crosses the first contact surface.

(2)

The information processing device according to (1) described above, in which at least one of the number of, a position of, a direction of, or a shape of the groove is set on the basis of at least one of a shape of the first contact surface, a portion of the user to be brought into contact with the first contact surface, a position and a direction of the first contact surface with respect to the portion, a movement of the portion, or a direction of force at the portion.

(3)

The information processing device according to (2) described above, in which
- the first contact surface has a rectangular shape, and
- the groove crosses between two sides of the first contact surface in a longitudinal direction.

(4)

The information processing device according to (2) or (3) described above, in which
- the first contact surface includes a raised portion, and
- the groove is formed along at least a portion of a periphery of the raised portion.

(5)

The information processing device according to any one of (2) to (4) described above, in which
- the information processing device is to be worn on an arm of the user, and
- the groove crosses the first contact surface in a direction in which the arm extends.

(6)

The information processing device according to any one of (2) to (5) described above, in which
- the information processing device is to be worn on a wrist of the user, and
- the groove includes two grooves having end portions, the end portions being disposed on a side of the first contact surface on a back side of a hand of the user and being disposed at positions spaced apart from a middle of the side and in directions differing from each other.

(7)

The information processing device according to any one of (2) to (6) described above, in which the groove includes two grooves having end portions, the end portions being disposed on a side of the first contact surface and being disposed at positions spaced apart from a middle of the side and in directions differing from each other, the side being a side into which sweat flows in a state in which the user wears the information processing device.

(8)

The information processing device according to any one of (2) to (7) described above, in which, in a case where the portion moves in a predetermined manner, the direction of the groove is set on the basis of a direction of force acting at the portion.

(9)

The information processing device according to any one of (1) to (8) described above, further including a wearing unit that allows the information processing device to be worn, in which
- at least a portion of a periphery of the first contact surface is surrounded by a second contact surface of the wearing unit, the second contact surface being brought into contact with the skin of the user, and
- the groove crosses the first contact surface and the second contact surface.

(10)

The information processing device according to any one of (1) to (9) described above, in which at least one of a position, a direction, or a shape of the groove is variable.

(11)

The information processing device according to (10) described above, further including:
- a first member provided on the first contact surface and having a shape that is changeable in a direction parallel to the first contact surface, and
- a second member provided on the first contact surface with a predetermined space being provided from the first member, and having a shape that is changeable in the direction parallel to the first contact surface, in which
- the groove includes a space provided between the first member and the second member.

(12)

The information processing device according to (11) described above, in which the first member and the second member are able to expand and contract, or inflate and shrink, in the direction parallel to the first contact surface.

(13)

The information processing device according to any one of (10) to (12) described above, including:
- a detecting unit that detects a state of a portion of the user, the information processing device being worn on the portion, and
- a controller that controls at least one of the position, the direction, or the shape of the groove, on the basis of the state of the portion.

(14)

The information processing device according to any one of (1) to (13) described above, in which the first contact surface is replaceable.

(15)

The information processing device according to any one of (1) to (14) described above, further including a mechanism that adjusts a barometric pressure in the groove.

(16)

The information processing device according to any one of (1) to (15) described above, further including a mechanism that adjusts a distribution of a temperature in the groove.

(17)

The information processing device according to any one of (1) to (16) described above, in which the first contact surface includes diatomaceous earth.

(18)

The information processing device according to any one of (1) to (17) described above, in which the first contact surface has a lotus effect.

(19)

The information processing device according to any one of (1) to (18) described above, in which the main body portion includes a sensor that detects biological information related to a surface of the skin of the user or related to inside of the skin of the user.

(20)

A method of ventilating an information processing device, the method including providing, on a contact surface of the information processing device to be worn by a user, a groove that crosses the contact surface, the contact surface being brought into contact with a skin of the user.

DESCRIPTION OF REFERENCE CHARACTERS 10 wearable device, 11 device section, 11A raised portion, 11B contact surface, 12 band, 51 to 211C groove, 300 wearable device, 301 device section, 301A raised portion, 302 band, 311*a*, 311*b* sheet, 312 coupling member, 313 groove, 361*a* to 361*d* sheet, 362, 363 coupling member, 364, 365 groove, 401*a*, 401*b* balloon, 401A groove, 402, 403 wall, 501 pipe, 521*a* to 521*d* balloon, 522 to 527 wall, 551 information processing unit, 561 detecting unit, 562 controller, 600 wearable device, 601 device section, 602 band, 611 groove, 630, 640 wearable device

The invention claimed is:

1. An information processing device to be worn by a user, the information processing device comprising:
a wearing unit configured to allow the information processing device to be worn;
a main body portion having a first contact surface that is brought into contact with a skin of the user; and
a groove that crosses the first contact surface, wherein
at least a portion of a periphery of the first contact surface is surrounded by a second contact surface of the wearing unit,
the second contact surface is brought into contact with the skin of the user, and
the groove crosses the first contact surface and the second contact surface.

2. The information processing device according to claim 1, wherein
at least one of a number of, a position of, a direction of, or a shape of the groove is set based on at least one of a shape of the first contact surface, a portion of the user to be brought into contact with the first contact surface, a position and a direction of the first contact surface with respect to the portion, a movement of the portion, or a direction of force at the portion.

3. The information processing device according to claim 2, wherein
the first contact surface has a rectangular shape, and
the groove crosses between two sides of the first contact surface in a longitudinal direction.

4. The information processing device according to claim 2, wherein
the first contact surface includes a raised portion, and
the groove is along at least a portion of a periphery of the raised portion.

5. The information processing device according to claim 2, wherein
the information processing device is to be worn on an arm of the user, and
the groove crosses the first contact surface in a direction in which the arm extends.

6. The information processing device according to claim 2, wherein
the information processing device is to be worn on a wrist of the user, and
the groove comprises two grooves having end portions, wherein
the end portions are on a side of the first contact surface on a back side of a hand of the user, and
the end portions are at positions spaced apart from a middle of the side and in directions differing from each other.

7. The information processing device according to claim 2, wherein
the groove comprises two grooves having end portions, the end portions are on a side of the first contact surface and are at positions spaced apart from a middle of the side and in directions differing from each other, and
the side is a side into which sweat flows in a state in which the user wears the information processing device.

8. The information processing device according to claim 2, wherein, based on a movement of the portion in a specific manner, the direction of the groove is set based on a direction of force acting at the portion.

9. The information processing device according to claim 1, wherein at least one of a position, a direction, or a shape of the groove is variable.

10. The information processing device according to claim 9, further comprising:
a first member on the first contact surface, wherein shape of the first member is changeable in a direction parallel to the first contact surface; and
a second member on the first contact surface, wherein
the second member is spaced apart from the first member, and
a shape of the second member is changeable in the direction parallel to the first contact surface, wherein
the groove comprises a space between the first member and the second member.

11. The information processing device according to claim 10, wherein
the first member and the second member are configured to expand and contract, or inflate and shrink, in the direction parallel to the first contact surface.

12. The information processing device according to claim 9, further comprising:
a detecting unit configured to detect a state of a portion of the user, wherein the information processing device is worn on the portion; and
a controller configured to control at least one of the position, the direction, or the shape of the groove based on the state of the portion.

13. The information processing device according to claim 1, wherein the first contact surface is replaceable.

14. The information processing device according to claim 1, further comprising a mechanism configured to adjust a barometric pressure in the groove.

15. The information processing device according to claim 1, further comprising a mechanism configured to adjust a distribution of a temperature in the groove.

16. The information processing device according to claim 1, wherein the first contact surface includes diatomaceous earth.

17. The information processing device according to claim 1, wherein the first contact surface has a lotus effect.

18. The information processing device according to claim 1, wherein the main body portion includes a sensor configured to detect biological information related to at least one of a surface of the skin of the user or inside of the skin of the user.

19. A method of ventilating an information processing device, the method comprising
providing a wearing unit that allows the information processing device to be worn by a user; and providing, on a first contact surface of the information processing device to be worn by the user, a groove that crosses the first contact surface, wherein
  the first contact surface is brought into contact with a skin of the user,
  at least a portion of a periphery of the first contact surface is surrounded by a second contact surface of the wearing unit,
  the second contact surface is brought into contact with the skin of the user, and
  the groove crosses the first contact surface and the second contact surface.

20. An information processing device to be worn by a user, the information processing device comprising:
  a main body portion having a contact surface that is brought into contact with a skin of the user;
  a groove that crosses the contact surface;
  a first member on the contact surface, wherein a shape of the first member is changeable in a direction parallel to the contact surface; and
  a second member on the contact surface, wherein
    the second member is spaced apart from the first member, and
    a shape of the second member is changeable in the direction parallel to the contact surface, wherein
    the groove comprises a space between the first member and the second member.

21. An information processing device to be worn by a user, the information processing device comprising:
  a main body portion having a contact surface that is brought into contact with a skin of the user;
  a groove that crosses the contact surface, wherein at least one of a position, a direction, or a shape of the groove is variable;
  a detecting unit configured to detect a state of a portion of the user, wherein the information processing device is worn on the portion; and
  a controller configured to control at least one of the position, the direction, or the shape of the groove based on the state of the portion.

* * * * *